(12) United States Patent
Aukerman et al.

(10) Patent No.: US 8,981,181 B2
(45) Date of Patent: Mar. 17, 2015

(54) MAIZE MICRORNA SEQUENCES

(75) Inventors: Milo Aukerman, Newark, DE (US); Hajime Sakai, Newark, DE (US); James Tisdall, Philadelphia, PA (US); Jeanne M. Wilson, Philadelphia, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/963,135

(22) Filed: Dec. 8, 2010

(65) Prior Publication Data

US 2011/0083232 A1 Apr. 7, 2011

Related U.S. Application Data

(62) Division of application No. 11/868,081, filed on Oct. 5, 2007, now abandoned.

(60) Provisional application No. 60/849,672, filed on Oct. 5, 2006.

(51) Int. Cl.
*C12N 15/113* (2010.01)
*C12N 15/82* (2006.01)

(52) U.S. Cl.
CPC .......... *C12N 15/8218* (2013.01); *C12N 15/113* (2013.01); *C12N 2310/111* (2013.01); *C12N 2310/14* (2013.01); *C12N 2310/53* (2013.01)
USPC ........................ 800/285; 435/320.1; 536/24.5

(58) Field of Classification Search
None
See application file for complete search history.

(56) References Cited

U.S. PATENT DOCUMENTS

2009/0093620 A1* 4/2009 Kovalic et al. ................ 536/23.1
2009/0293148 A1* 11/2009 Ren et al. ...................... 800/279

OTHER PUBLICATIONS

Schwab et al. (2006) Plant Cell 18: 1121-1133.*
Friedrich et al. (1982) J. Agric. Food Chem. 30: 192-193.*
Ishida et al. (1996) Nature Biotechnol. 14: 745-750.*
Whiteclaw et al. (2002) GenBank Accession No. BZ720359.*
TOPO TA Cloning Kit for Sequence (Invitrogen Life Technologies, copyright 2000-2002, version J, pp. 1-30).*
U.S. Appl. No. 10/963,238, filed Oct. 12, 2004, E. I. du Pont de Nemours and Company.
U.S. Appl. No. 10/963,394, filed Oct. 12, 2004, E. I. du Pont de Nemours and Company.
U.S. Appl. No. 10/833,374, filed Jul. 1, 2004, Patrick Lad et al.
U.S. Appl. No. 10/913,288, filed Aug. 6, 2004, Whitehead Institute for Biomedical Research.
U.S. Appl. No. 11/334,776, filed Jan. 6, 2006, State of Oregon.
Allen et al., Microrna-Directed Phasing During Trans-Acting Sirna Biogenesis in Plants, Cell, 2005, vol. 121:207-221.
Allshire et al., RNAI and Heterochromatin—A Hushed-Up Affair, Science, 2002, vol. 297:1818-1819.
Aukerman et al., Regulation of Flowering Time and Floral Organ Identity by a Microrna and Its APETALA2-Like Target Genes, Plant Cell, 2003, vol. 15:2730-2741.
Axtell et al., Antiquity of Micrornas and Their Targets in Land Plants, Plant Cell 2005, vol. 17:1658-1673.
Bartel., Mcirornas: Genomics, Biogenesis, Mechanism, and Function, Cell 2004, vol. 116:281-297.
Berstein et al., Role for Bidentate Ribonuclease in the Initiation Step of RNA Interface, Nature, 2001, vol. 409:363-366.
Bonnet et al., Tansley Review: The Small RNA World of Plants, New Phytol., 2006, vol. 171:451-468.
Buchman et al., Comparison of Intron-Dependent and Intron-Independent Gene Expression, Mol. Cell Biol., 1988, vol. 8:4395-4405.
Call Is et al., Introns Increase Gene Expression in Cultured Maize Cells, Genes Dev., 1987, vol. 1:1183-1200.
Database EMBL, Aug. 28, 2003, PUKA075TB *Zea mays* genomic clone ZMMBTa0775N05, genomic survey sequence, Database Accession No. CG111078.
Davison et al., Analyzing Micro-RNA Expression Using Microarrays, Methods in Enzymology, 2006, vol. 411:14-34.
Elbashir et al., Duplexes F 21-Nucleotide RNAS Mediate RNA Interference in Cultured Mammalian Cells, Nature, 2001, vol. 411:494-498.
Elbashir et al., RNA Interference is Mediated by 21- and 22-Nucleotide RNAS, Genes Dev., 2001, vol. 15:18B.
Fire et al., Potent and Specific Genetic Interference by Double-Stranded RNA in *Caenorhabditis elegans*, Nature, 1998, vol. 391:806-611.
Fire et al., RNA-Triggered Gene Silencing, Trends Genet., 1999, vol. 15:358-363.
Griffiths-Jones, Mirbase: Microrna Sequences, Targets and Gene Nomenclature, Nuc. Acids. Res., 2006, vol. 34:140-144.
Grishok et al., Genes and Mechanisms Related to RNA Interference Regulate Expression of the Small Temporal RNAS That Control *C. elegans* Developmental Timing, Cell, 2001, vol. 106:23-34.
Hall et al.. Establishment and Maintenance of a Heterochromatin Domain, Science, 2002, vol. 297:2232-2237.
Hammond et al., An RNA-Directed Nuclease Mediates Post-Transcriptional Gene Silencing in *Drosophila* Cells, Nature, 2000, vol. 404:293-296.
Hutvagner et al., A Cellular Function for the RNA-Interference Enzyme Dicer in the Maturation of the Let-7 Small Temporal RNA, Science, 2001, vol. 293:834-838.
Hutvagner et al., A Microrna in a Multiple-Turnover RNAI Enzyme Complex, Science, 2002, vol. 297:2056-2060.
Jenuwein et al., An RNA-Guided Pathway for the Epigenome, Science, 2002, vol. 297:2215-2218.
Johnson et al., CSRDB: A Small RNA Integrated Database and Browser Resource for Cereals, Nuc. Acids Res., 2007, vol. 35:829-833.
Jones-Rhoades et al., Computational Identification of Plant Micrornas and Their Targets, Including a Stress-Induced Mirna, Mol. Cell, 2004, vol. 14:787-799.

(Continued)

*Primary Examiner* — David T Fox
*Assistant Examiner* — Steven Bernacki

(57) ABSTRACT

Methods and compositions useful in target sequence suppression and target sequence validation are described. Polynucleotide constructs useful for gene silencing, as well as cells, plants and seeds comprising the polynucleotides and a method for using microRNAs to silence a target sequence are also described.

4 Claims, No Drawings

(56) References Cited

OTHER PUBLICATIONS

Ketting et al., Dicer Functions in RNA Interference and in Synthesis of Small RNA Involved in Developmental Timing in *C. elegans*, Genes Dev., 2001, vol. 15:2654-2659.

Kurihara et al., Arabidopsis Micro-RNA Biogenesis Through Dicer-Like 1 Protein Functions, Proc. Natl. Acad. Sci., 2004, vol. 101:12753-12758.

Lagos-Quintana et al., Identification of Novel Genes Coding for Small Expressed RNAS, Science, 2001, vol. 294:853-858.

Lagos-Quintana et al., Identification of Tissue-Specific Micrornas From Mouse, Curr. Biol., 2002, vol. 12:735.739.

Lau et al., An Abundant Class of Tiny RNAS With Probable Regulatory Roles in *Caenorhabditis elegans*, Science, 2001, vol. 294:858-862.

Lee et al., An Extensive Class of Small RNAS in *Caenorhabditis elegans*, Science, 2001, vol. 294:862-864.

Lee et al., Microrna Maturation: Stepwise Processing and Subcellular Localization, Embo J., 2002, vol. 21:4663-4670.

Lee et al., The *C. elegans* Heterochronic Gene Lin-4 Encodes Small RNAS With Antisense Complementarity to Lin-14, Cell, 1993, vol. 75:843-854.

Llave et al., Cleavage of Scarecrow-Like MRNA Targets Directed by a Class of *Arabidopsis*, Science, vol. 297:2053-2056.

Llave et al., Endogenous and Silencing-Associated Small RNAS in Plants, Plant Cell, 2002, vol. 14:1605-1619.

Luck, Normalization and Error Estimation for Biomolecular Expression Patterns, Proceedings of SPIE, 2001, vol. 4266:153-157.

Mallory et al., Functions of Micrornas and Related Small RNAS in Plants, Natl. Genet., 2006, vol. 38:31-36.

Meyers et al, Sweating the Small Stuff: Microrna Discovery in Plants, Curr. Opin. Biotech., 2006, vol. 17:1-8.

Mica Erica at al., Characterization of five microRNA families in maize, Journal of Experimental Botany. vol. 57(11), pp. 2601-2612, 2006.

Mourelatos et al., MIRNPS: A Novel Class of Ribonucleoproteins Containing Numerous Micrornas, Genes Dev., 2002, vol, 16:720-728.

Parizotto et al., In Vitro Investigation of the Transcription, Processing, Endonucleolytic Activity, and Functional Relevance of the Spatial Distribution of a Plant Mirna, Genes Dev., 2004, vol. 18:2237-2242.

Park et al., Carpel Factory, A Dicer Homolog, and Hens, A Novel Protein, Act in Microrna Metabolism in *Arabidopsis thaliana*, Curr. Biol., 2002, vol, 12:1484-1495.

Reinhart et al., Micrornas in Plants, Genes Dev., 2002, vol. 16:1616-1626.

Reinhart et al., The 21-Nucleotide Let-7 RNA Regulates Developmental Timing in *Caenorhabditis*, Nature, 2000, vol. 403:901-906.

Rhoaides et al., Prediction of Plant Microrna Targets, Cell, 2002, vol. 110:513-620.

Schwartz et al., Asymmetry in the Assembly of the RNAI Enzyme Complex, Cell, 2003, vol. 115:199-208.

Shi et al., Facile Means for Quantifying Microrna Expression by Real-Time PCR, Biotechniques, 2005, vol. 39:519-525.

Slack et al., The Lin-41 RBCC Gene Acts in the *C. elegans* Heterochronic Pathway Between the Let-7 Regulatory RNA and the Lin-29 Transcription Factor, Mol. Cell, 2000, vol. 5:659-669.

Sunkar et al., Cloning and Characterization of Micrornas From Rice, The Plant Cell, 2005, vol. 17:1397-1411.

Sunkar et al., Novel and Stress-Regulated Micrornaa and Other Small RNAS From *Arabidopsis*, Plant Cell, 2004, vol. 16:2001-2019.

Van Eenennaam et al., Plant Cell, 2003, vol. 15, p. 3007-3019.

Volpe et al., Regulation of Heterochromatic Silencing and Histone H3 Lysine-9 Methylation by RNA1, Science, 2002, vol. 297:1833-1837.

Wianny et al., Specific Interference With Gene Function by Double-Stranded RNA in Early Mouse Development, Nature Cell Biol., 1999, vol. 2:70-75.

Wightman et al., Posttranscriptional Regulation of the Heterochronic Gene Lin-14 by Lin-4 Mediates Temporal Pattern Formation in *C. elegans*, Cell, 1993, vol. 75:855-862.

Zhang et al., Identification of 188 Conserved Maize RNAS and Their Targets, FEBS Lett., 2006, vol. 580:3753-3762.

Database EMBL [Online] Mar. 19, 2003,"PUGFE74TD ZM 0.6_1.0_KB *Zea mays* genomic clone ZMMBTA370NO3, DNA Sequence.", XP002712519, retrieved from EBI Accession No. EM_GSS:BZ786669 Database Accession No. BZ786669.

Database EMBL [Online] Jul. 19, 2004, "3530_1_203_1_E05.y_1 3530—Full length cDNA library created by Invitrogen from multiple tissues *Zea mays* cDNA, mRNA Sequence"., XP002712520, retrieved from EBI Accession No. EM_EST:C0530846, Database Accession No. C0530846.

Corresponding European Search Report on Application No. 13162637.6, Dated Jan. 22, 2014.

Juarez, M.T., et al., "microRNA-mediated repression of *rolled leafl* species maize leaf polarity," *Nature*, vol. 428, pp. 84-88 (Mar. 2004).

Lauter, N., et al., "*microRNA172* down-regulates *glossy15* to promote vegetative phase change in maize," *PNAS*, vol. 102, No. 26, pp. 9412-9417 (Jun. 2005).

\* cited by examiner

MAIZE MICRORNA SEQUENCES

CROSS REFERENCE TO RELATED APPLICATIONS

This is a divisional application of U.S. Utility application Ser. No. 11/868,081 filed Oct. 5, 2007, which claims the benefit of U.S. Provisional Application No. 60/849,672, filed Oct. 5, 2006, both of which are herein incorporated by reference in their entirety.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 399455SEQLIST.txt, created on Dec. 8, 2010, and having a size of 1,560 kilobytes and is filed concurrently with the specification. The sequence listing contained in this ASCII formatted document is part of the specification and is herein incorporated by reference in its entirety.

FIELD OF THE INVENTION

The field of the present invention relates generally to plant molecular biology. More specifically it relates to constructs and methods to suppress the expression of targeted genes.

BACKGROUND

MicroRNAs (miRNAs) were first identified only a few years ago, but already it is clear that they play an important role in regulating gene activity. These 20-22 nucleotide non-coding RNAs have the ability to hybridize via base-pairing with specific target mRNAs and downregulate the expression of these transcripts, by mediating either RNA cleavage or translational repression. Recent studies have indicated that miRNAs have important functions during development. In plants, they have been shown to control a variety of developmental processes including flowering time, leaf morphology, organ polarity, floral morphology, and root development (reviewed by Mallory and Vaucheret (2006) *Nat Genet* 38: S31-36). Given the established regulatory role of miRNAs, it is likely that they are also involved in the control of some of the major crop traits such drought tolerance and disease resistance.

Plant miRNAs are processed from longer precursor transcripts termed pre-miRNA that range in length from ~50 to 500 nucleotides, and these precursors have the ability to form stable hairpin structures (reviewed by Bartel (2004) *Cell* 116: 281-297). Many miRNA hairpin precursors originate as longer transcripts of 1-2 kb or longer, termed pri-miRNA, that are polyadenylated and capped. This fact coupled with the detection of numerous pri-miRNAs in Expressed Sequence Tags (ESTs) libraries indicates that RNA polymerase II is the enzyme responsible for miRNA gene transcription. Transgenic experiments indicate that it is the structure rather than the sequence of the pre-miRNA that directs their correct processing and that the rest of the pri-miRNA is not required for the production of miRNAs. While pri-miRNAs are processed to pre-miRNAs by Drosha in the nucleus and Dicer cleaves pre-miRNAs in the cytoplasm in metazoans, miRNA maturation in plants differs from the pathway in animals because plants lack a Drosha homolog. Instead, the RNase III enzyme DICER-LIKE 1 (DCL1), which is homologous to animal Dicer, may possess Drosha function in addition to its known function in hairpin processing (Kurihara and Watanabe (2004) *Proc Natl Acad Sci* 101: 12753-12758).

Through the cloning efforts of several labs, at least 30 miRNA families have been identified in *Arabidopsis* (reviewed by Meyers et al. (2006) *Curr Opin Biotech* 17; 1-8). Many of these miRNA sequences are represented by more than one locus, bringing the total number up to approximately 100. Because the particular miRNAs found by one lab are not generally overlapping with those found by another independent lab, it is assumed that the search for the entire set of miRNAs expressed by a given plant genome, the "miR-Nome," is not yet complete. One reason for this might be that many miRNAs are expressed only under very specific conditions, and thus may have been missed by standard cloning efforts. A recent study by Sunkar and Zhu (2004, *Plant Cell* 16: 2001-2019) suggests that, indeed, miRNA discovery may be facilitated by choosing "non-standard" growth conditions for library construction. Sunkar and Zhu identified novel miRNAs in a library consisting of a variety of stress-induced tissues. They proceeded to demonstrate induction of some of these miRNAs by drought, cold and other stresses, suggesting a role for miRNAs in stress response. It is likely, then, that efforts to fully characterize the plant miRNome will require examination of the small RNA profile in many different tissues and under many different conditions.

A complementary approach to standard miRNA cloning is computational prediction of miRNAs using available genomic and/or EST sequences, and several labs have reported finding novel *Arabidopsis* miRNAs in this manner (reviewed by Bonnet et al. (2006) *New Phytol* 171:451-468). Using these computational approaches, which rely in part on the observation that known miRNAs reside in hairpin precursors, hundreds of plant miRNAs have been predicted. However only a small fraction have been experimentally verified by Northern blot analysis. In addition, most of these computational methods rely on comparisons between two representative genomes (e.g. *Arabidopsis* and rice) in order to find conserved intergenic regions, and thus are not suitable for identifying species-specific miRNAs, which may represent a substantial fraction of the miRNome of any given organism.

Computational methods have also facilitated the prediction of miRNA targets, and in general plant miRNAs share a high degree of complementarity with their targets (reviewed by Bonnet et al. (2006) *New Phytol* 171:451-468). The predicted mRNA targets of plant miRNAs encode a wide variety of proteins. Many of these proteins are transcription factors and are thus likely to be important for development. However, there are also many enzymes that are putatively targeted, and these potentially have roles in such processes as mitochondrial metabolism, oxidative stress response, proteasome function, and lignification. It is likely that this list of processes regulated by miRNA will get longer as additional miRNAs are identified, and that eventually miRNAs will be implicated in processes critical to crop improvement. For example, a recently identified miRNA targeting genes in the sulfur assimilation pathway was identified, and shown to be induced under conditions of sulfate starvation (Jones-Rhoades and Bartel (2004) *Mol Cell* 14: 787-799). This particular miRNA, then, is a candidate gene for increasing sulfur assimilation efficiency. It is tempting to speculate that the pathways for assimilating other compounds such as water and nitrate may also be under miRNA control.

Much of the work on identification of novel miRNAs has been carried out in the model system *Arabidopsis*, and thus miRNomes of crop plants such as maize, rice and soybean are less fully understood. There is also no complete genome sequence available for crops such as maize and soybeans, further hampering miRNome analysis. Many *Arabidopsis* miRNAs have homologs in these other species, however there are also miRNAs that appear to be specific to *Arabidopsis*. Likewise, it is expected that there will be nonconserved miRNAs specific to the aforementioned crop species. A significant fraction of the non-conserved miRNAs could be part of the regulatory networks associated with species-specific growth conditions or developmental processes. As such, it is crucial to carry out miRNA cloning in crop species such as maize, to complement the bioinformatic approaches currently being used, and ultimately to more fully characterize the miRNomes of crop species.

BRIEF DESCRIPTION OF THE TABLES

TABLE 1

The table of putative miRNAs consists of 2808 rows of 6 columns, which are

1: ID: a unique ID number, which represents the SEQ ID NO for the corresponding microRNA (miRNA) in that row
2: miRNA: the 21 nucleotide maize microRNA sequence
3: TARGETSEQ: the exact complement of the miRNA that corresponds to one potential site for cleavage on the target mRNA
4: BACKBONE: the genomic DNA sequence that forms a hairpin structure incorporating the miRNA sequence
5: FOLD: secondary structure information for the backbone sequences based on context free grammar of nested parentheses, where a "(" represents a nucleotide that hybridizes with a down stream nucleotide denoted by a ")", and a "." represents an unpaired nucleotide the resulting structure displays the hairpin structure formed by the backbone
6: TARGET: public ID(s) of possible genomic targets of the miRNA, databases that were searched included rice genes from the TIGR Version 4 rice datasets all.cds and all_small_genes.cds; and the TIGR maize gene index file ZMGI.101205.

TABLE 4

The table of small RNA expression data for maize microRNAs of the present invention and public domain *Zea mays* microRNAs consists of 2702 rows of 18 columns, which are 1: ID: a unique ID number, which represents the SEQ ID NO for the corresponding putative microRNA (miRNA) in that row, or the public domain *Zea mays* names associated with the miRNA sequence in that row
2: MIRNACORE: the ~21 nucleotide maize microRNA sequence, also referred to as the "query sequence"
3. CALL B73_LEAF: the detectability assessment applied to the miRNA in that row based on its corresponding expression profiling measurements in RNA samples derived from B73 leaf tissue. "PASSED," "ENRICHED" or "HIGHLY ENRICHED" were applied only if the array data for that miRNA met the specificity, reproducibility and signal strength criteria in Table 3. "ENRICHED" was applied to miRNAs showing between 5-fold and 10-fold more perfectly sequence matched (0 MM) probe signal intensity in B73 leaf samples than in other samples in the same experiment. "HIGHLY ENRICHED" was applied to miRNAs showing 10-fold more 0 MM-probe signal intensity in B73 leaf samples than in other samples in the same experiment. Sample B73 Leaf and all other samples are described in Table 2
4. 0 MM B73_LEAF: the normalized fluorescence intensity score of the perfectly sequence matched probe of the miRNA in that row as measured in expression profiling of genotype B73 leaf RNA.
5. CALL B73_EAR: the detectability assessment applied to the miRNA in that row based on its corresponding expression profiling measurements in RNA samples derived from B73 ear tissue.
6. 0 MM B73_EAR: the normalized fluorescence intensity score of the perfectly sequence matched probe of the miRNA in that row as measured in expression profiling of genotype B73 ear RNA.
7. CALL B73_SEEDLING: the detectability assessment applied to the miRNA in that row based on its corresponding expression profiling measurements in RNA samples derived from B73 seedling tissue.
8. 0 MM B73_SEEDLING: the normalized fluorescence intensity score of the perfectly sequence matched probe of the miRNA in that row as TABLE 4-continued The table of small RNA expression data for maize microRNAs of the present invention and public domain *Zea mays* microRNAs consists of 2702 rows of 18 columns, which are measured in expression profiling of genotype B73 seedling RNA.
9. CALL 3245_Normal_N: the detectability assessment applied to the miRNA in that row based on its corresponding expression profiling measurements in RNA samples derived from 3245 leaf tissue grown in fields with normal levels of nitrogen.
10. 0 MM 3245_Normal_N: the normalized fluorescence intensity score of the perfectly sequence matched probe of the miRNA in that row as measured in expression profiling of RNA from leaves of genotype 3245 plants grown in fields with normal levels of nitrogen.
11. CALL 3245_Low_N: the detectability assessment applied to the miRNA in that row based on its corresponding expression profiling measurements in RNA samples derived from 3245 leaf tissue grown in fields with low levels of nitrogen.
12. 0 MM 3245_Low_N: the normalized fluorescence intensity score of the perfectly sequence matched probe of the miRNA in that row as measured in expression profiling of RNA from leaves of genotype 3245 plants grown in fields with low levels of nitrogen.
13. CALL 33B50_Low_N: the detectability assessment applied to the miRNA in that row based on its corresponding expression profiling measurements in RNA samples derived from 33B50 leaf tissue grown in fields with low levels of nitrogen.
14. 0 MM 33B50_Low_N: the normalized fluorescence intensity score of the perfectly sequence matched probe of the miRNA in that row as measured in expression profiling of RNA from leaves of genotype 33B50 plants grown in fields with low levels of nitrogen.
15. CALL B73_Low_N: the detectability assessment applied to the miRNA in that row based on its corresponding expression profiling measurements in RNA samples derived from B73 leaf tissue grown with minimal nitrogen supplementation.
16. 0 MM B73_Low_N: the normalized fluorescence intensity score of the perfectly sequence matched probe of the miRNA in that row as measured in expression profiling of RNA from leaves of genotype B73 plants grown with minimal nitrogen supplementation.
17: TARGETSEQ: the exact complement of the miRNA that corresponds to one potential site for cleavage on the target mRNA
18: TARGET: public ID(s) of possible genomic targets of the putative miRNA, databases that were searched included rice genes from the TIGR Version 4 rice datasets all.cds and all_small_genes.cds; and the TIGR maize gene index file ZMGI.101205.

BRIEF DESCRIPTION OF THE SEQUENCE LISTING

A Sequence Listing and Table are provided herewith on Compact Disk. The contents of the Compact Disk containing the Sequence Listing and Table are hereby incorporated by reference in compliance with 37 CFR 1.52(e). The Compact Disks are submitted in triplicate and are identical to one another. The disks are labeled "Copy 1—Sequence Listing and Table", "Copy 2—Sequence Listing and Table", and CRF. The disks contain the following files: BB1593 US PRV Sequence Listing having the following size: 1,471,000 bytes and BB1593 US PRV Table having the following size: 4,430,000 bytes which were created Oct. 5, 2006.

SEQ ID NOs: 1-2652 represent individual 21 nucleotide microRNA sequences from maize. The individual microRNAs are shown in Table 1 as the "miRNAcore" column (column 2), the SEQ ID NO for each sequence is shown in column 1 (ID) of Table 1.

SEQ ID NOs: 2653-5304 represent the complement of SEQ ID NOs:1-2652, also shown as "targetseq" in column 3 of Table 1.

SEQ ID NOs:5305-7956 represent the "backbone" hairpin sequence that surrounds the miRNAs in SEQ ID NOs:1-2652, respectively, in the maize genome. This information can also be found in column 4 of Table 1.

SEQ ID NO:7957 is a sequential concatenation of all 21 nucleotide miRNAs found in SEQ ID NOs:1-2652

(21×2652=55,692). It is believed that this representative example is one of many different forms that are useful for altering plant gene expression. Other examples would include different ordering of the individual miRNA sequences, duplication of certain miRNA sequences, elimination of certain miRNA sequences, and altered spacing in between the miRNA sequences.

SEQ ID NO:7958 is a 21 nucleotide sequence complementary to the *Arabidopsis* fatty acid desaturase 2 (FAD2) gene.

SEQ ID NOs: 7959-8114 represent individual 21 nucleotide microRNA sequences from maize. The individual microRNAs are shown in Table 1 as the "miRNAcore" column (column 2), the SEQ ID NO for each sequence is shown in column 1 (ID) of Table 1.

SEQ ID NOs: 8115-8270 represent the complement of SEQ ID NOs:7959-8114, also shown as "targetseq" in column 3 of Table 1.

SEQ ID NOs:8271-8426 represent the "backbone" hairpin sequence that surrounds the miRNAs in SEQ ID NOs:7959-8114, respectively, in the maize genome. This information can also be found in column 4 of Table 1.

SEQ ID NO:8427 is a sequential concatenation of all 21 nucleotide miRNAs found in SEQ ID NOs:7959-8114 (21× 156=3,276). It is believed that this representative example is one of many different forms that are useful for altering plant gene expression. Other examples would include different ordering of the individual miRNA sequences, duplication of certain miRNA sequences, elimination of certain miRNA sequences, and altered spacing in between the miRNA sequences.

SEQ ID NOs:8428-8429 are RNA adaptors sequences.

SUMMARY OF THE INVENTION

The present invention relates, inter alia, to an isolated polynucleotide comprising: a microRNA selected from the group consisting of SEQ ID NOs:1-2652 and SEQ ID NOs:7959-8114.

In a second embodiment, the invention relates to a full-length complement of the microRNA selected from the group consisting of SEQ ID NOs:1-2652 and SEQ ID NOs:7959-8114 or a nucleotide sequence capable of hybridizing to these aforemention microRNAs. wherein the hybridizable nucleotide sequence comprises at least 21 nucleotides.

In a third embodiment, the invention relates to an isolated polynucleotide useful for altering plant gene expression comprising SEQ ID NO:7957 or SEQ ID NO:8427 wherein said isolated polynucleotide comprises at least one functional domain having at least 21(x) contiguous nucleotides and x is an integer from 1 to 2652, further wherein said nucleotides start at nucleotide 1 or any nucleotide 21(x)+1.

In a fourth embodiment, the invention relates to a functional subdomain of such isolated polynucleotides, wherein said functional subdomain comprises at least one microRNA.

In a fifth embodiment, the invention relates to an isolated polynucleotide comprising a microRNA containing sequence selected from the group consisting of SEQ ID NOs: 5305-7956 and SEQ ID NOs:8271-8426.

In a sixth embodiment, the invention relates to a DNA expression construct comprising any of the isolated polynucleotides discussed herein operably linked to at least one regulatory sequence.

In a seventh embodiment, the invention relates to a plant comprising in its genome the DNA expression constructs discussed herein. Such plants can be selected from the group consisting of corn, rice, sorghum, sunflower, millet, soybean, canola, wheat, barley, oat, beans, and nuts.

In an eighth embodiment, the invention relates to transgenic seeds obtained from a plant comprising in its genome the DNA expression constructs discussed herein. Also within the scope of the invention are transformed plant tissue or a plant cell comprising in its genome the DNA expression constructs discussed herein.

In an ninth embodiment, the invention relates to by-products obtained from such transgenic seeds or to progeny plants obtained from such transgenic seeds.

In a tenth embodiment, the invention relates to a method for altering expression of a stably introduced nucleotide sequence in a plant comprising:
a) making a DNA expression construct comprising a stably introduced nucleotide sequence and at least one sequence capable of hybridizing to the isolated polynucleotide of the invention;
b) transforming a plant with the DNA expression construct of part (a); and
c) selecting a transformed plant which comprises the DNA expression construct of part (a) in its genome and which has altered expression of the stably introduced nucleotide sequence when compared to a plant transformed with a modified version of the DNA expression construct of part (a) wherein the modified construct lacks the sequence capable of hybridizing to the isolated polynucleotide of the invention.

DETAILED DESCRIPTION

Information pertinent to this application can be found in U.S. patent application Ser. Nos. 10/963,238 and 10/963,394, filed Oct. 12, 2004. The entire contents of the above applications are herein incorporated by reference.

Other references that may be useful in understanding the invention include U.S. patent application Ser. No. 10/883, 374, filed Jul. 1, 2004; U.S. patent application Ser. No. 10/913,288, filed Aug. 6, 2004; and U.S. patent application Ser. No. 11/334,776, filed Jan. 6, 2006.

Recently discovered small RNAs play an important role in controlling gene expression. Regulation of many developmental processes including flowering is controlled by small RNAs. It is now possible to engineer changes in gene expression of plant genes by using transgenic constructs which produce small RNAs in the plant.

The invention provides methods and compositions useful for suppressing targeted sequences. The compositions can be employed in any type of plant cell, and in other cells which comprise the appropriate processing components (e.g., RNA interference components), including invertebrate and vertebrate animal cells. The compositions and methods are based on an endogenous miRNA silencing process discovered in *Arabidopsis*, a similar strategy can be used to extend the number of compositions and the organisms in which the methods are used. The methods can be adapted to work in any eukaryotic cell system. Additionally, the compositions and methods described herein can be used in individual cells, cells or tissue in culture, or in vivo in organisms, or in organs or other portions of organisms.

The compositions selectively suppress the target sequence by encoding a miRNA having substantial complementarity to a region of the target sequence. The miRNA is provided in a nucleic acid construct which, when transcribed into RNA, is predicted to form a hairpin structure which is processed by the cell to generate the miRNA, which then suppresses expression of the target sequence.

Nucleic acid sequences are disclosed that encode miRNAs from maize. Backbone hairpins containing the individual miRNA sequences are also disclosed. Constructs are described for transgenic expression of miRNAs and their backbones. Alternatively, constructs are described wherein backbone sequences and miRNA sequences are exchanged thereby altering the expression pattern of the miRNA, and its subsequent specific target sequence in the transgenic host. Any miRNA can be exchanged with any other backbone to create a new miRNA/backbone hybrid.

A method for suppressing a target sequence is provided. The method employs any of the constructs above, in which a miRNA is designed to identify a region of the target sequence, and inserted into the construct. Upon introduction into a cell, the miRNA produced suppresses expression of the targeted sequence. The target sequence can be an endogenous plant sequence, or a heterologous transgene in the plant.

There can also be mentioned as the target gene, for example, a gene from a plant pathogen, such as a pathogenic virus, nematode, insect, or mold or fungus.

Another aspect of the invention concerns a plant, cell, and seed comprising the construct and/or the miRNA. Typically, the cell will be a cell from a plant, but other prokaryotic or eukaryotic cells are also contemplated, including but not limited to viral, bacterial, yeast, insect, nematode, or animal cells. Plant cells include cells from monocots and dicots. The invention also provides plants and seeds comprising the construct and/or the miRNA.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

The term "plant parts" includes differentiated and undifferentiated tissues including, but not limited to the following: roots, stems, shoots, leaves, pollen, seeds, tumor tissue and various forms of cells and culture (e.g., single cells, protoplasts, embryos and callus tissue). The plant tissue may be in plant or in a plant organ, tissue or cell culture.

The term "plant organ" refers to plant tissue or group of tissues that constitute a morphologically and functionally distinct part of a plant.

The term "genome" refers to the following: (1) the entire complement of genetic material (genes and non-coding sequences) present in each cell of an organism, or virus or organelle; (2) a complete set of chromosomes inherited as a (haploid) unit from one parent.

"Progeny" comprises any subsequent generation of a plant. Progeny will inherit, and stably segregate, genes and transgenes from its parent plant(s).

Units, prefixes, and symbols may be denoted in their SI accepted form. Unless otherwise indicated, nucleic acids are written left to right in 5' to 3' orientation; amino acid sequences are written left to right in amino to carboxyl orientation, respectively. Numeric ranges recited within the specification are inclusive of the numbers defining the range and include each integer within the defined range. Amino acids may be referred to herein by either commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5$^{th}$ edition, 1993). The terms defined below are more fully defined by reference to the specification as a whole.

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

This construct may comprise any combination of deoxyribonucleotides, ribonucleotides, and/or modified nucleotides. The construct may be transcribed to form an RNA, wherein the RNA may be capable of forming a double-stranded RNA and/or hairpin structure. This construct may be expressed in the cell, or isolated or synthetically produced. The construct may further comprise a promoter, or other sequences which facilitate manipulation or expression of the construct.

As used here "suppression" or "silencing" or "inhibition" are used interchangeably to denote the down-regulation of the expression of a product of a target sequence relative to its normal expression level in a wild type organism. Suppression includes expression that is decreased by about 10%, 15%, 20%, 25%, 30%, 35%, 40%, 45%, 50%, 55%, 60%, 65%, 70%, 75%, 80%, 85%, 90%, 95%, or 100% relative to the wild type expression level.

As used herein, "encodes" or "encoding" refers to a DNA sequence which can be processed to generate an RNA and/or polypeptide.

As used herein, "expression" or "expressing" refers to production of a functional product, such as, the generation of an RNA transcript from an introduced construct, an endogenous DNA sequence, or a stably incorporated heterologous DNA sequence. The term may also refer to a polypeptide produced from an mRNA generated from any of the above DNA precursors. Thus, expression of a nucleic acid fragment may refer to transcription of the nucleic acid fragment (e.g., transcription resulting in mRNA or other functional RNA) and/or translation of RNA into a precursor or mature protein (polypeptide).

As used herein, "heterologous" with respect to a sequence means a sequence that originates from a foreign species, or, if from the same species, is substantially modified from its native form in composition and/or genomic locus by deliberate human intervention. For example, with respect to a nucleic acid, it can be a nucleic acid that originates from a foreign species, or is synthetically designed, or, if from the same species, is substantially modified from its native form in composition and/or genomic locus by deliberate human intervention. A heterologous protein may originate from a foreign species or, if from the same species, is substantially modified from its original form by deliberate human intervention.

The term "host cell" refers to a cell which contains or into which is introduced a nucleic acid construct and supports the replication and/or expression of the construct. Host cells may be prokaryotic cells such as *E. coli*, or eukaryotic cells such as fungi, yeast, insect, amphibian, nematode, or mammalian cells. Alternatively, the host cells are monocotyledonous or dicotyledonous plant cells. An example of a monocotyledonous host cell is a maize host cell.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into ac ell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

The term "genome" as it applies to a plant cells encompasses not only chromosomal DNA found within the nucleus, but organelle DNA found within subcellular components (e.g., mitochondrial, plastid) of the cell.

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

As used herein, microRNA or "miRNA" refers to an oligoribonucleic acid, which regulates expression of a polynucleotide comprising the target sequence. A "mature miRNA" refers to the miRNA generated from the processing of a miRNA precursor. A "miRNA template" is an oligonucleotide region, or regions, in a nucleic acid construct which encodes the miRNA. The "backside" region of a miRNA is a portion of a polynucleotide construct which is substantially complementary to the miRNA template and is predicted to base pair with the miRNA template. The miRNA template and backside may form a double-stranded polynucleotide, including a hairpin structure.

As used herein, "domain" or "functional domain" refer to nucleic acid sequence(s) that are capable of eliciting a biological response in plants. The present invention concerns miRNAs composed of at least 21 nucleotide sequences acting either individually, or in concert with other miRNA sequences, therefore a domain could refer to either individual miRNAs or groups of miRNAs. Also, miRNA sequences associated with their backbone sequences could be considered domains useful for processing the miRNA into its active form. As used herein, "subdomains" or "functional subdomains" refer to subsequences of domains that are capable of eliciting a biological response in plants. A miRNA could be considered a subdomain of a backbone sequence. "Contiguous" sequences or domains refer to sequences that are sequentially linked without added nucleotides intervening between the domains. An example of a contiguous domain string is found in SEQ ID NO:7957 which represents SEQ ID NOs: 1-2652 as a continuous string that can be thought of as 2652 miRNA sequences linked together in a sequential concatenation.

As used herein, the phrases "target sequence" and "sequence of interest" are used interchangeably. Target sequence is used to mean the nucleic acid sequence that is selected for alteration (e.g., suppression) of expression, and is not limited to polynucleotides encoding polypeptides. The target sequence comprises a sequence that is substantially or fully complementary to the miRNA. The target sequence includes, but is not limited to, RNA, DNA, or a polynucleotide comprising the target sequence. As discussed in Bartel and Bartel (2003) Plant Phys. 132:709-719, most microRNA sequences are 20-22 nucleotides with anywhere from 0-3 mismatches when compared to their target sequences.

It is understood that microRNA sequences, such as the 21 nucleotide sequences of the present invention, may still be functional as shorter (20 nucleotide) or longer (22 nucleotide) sequences. In addition, some nucleotide substitutions, particularly at the last two nucleotides of the 3' end of the microRNA sequence, may be useful in retaining at least some microRNA function.

As used herein, "nucleic acid" means a polynucleotide and includes single or double-stranded polymer of deoxyribonucleotide or ribonucleotide bases. Nucleic acids may also include fragments and modified nucleotides. Thus, the terms "polynucleotide", "nucleic acid sequence", "nucleotide sequence" or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deosycytidylate, "G" for guanylate or deoxyguanylate, "U" for uridlate, "T" for deosythymidylate, "R" for purines (A or G), "Y" for pyrimidiens (C or T), "K" for G or T, "H" for A or C or T, "I" for inosine, and "N" for any nucleotide.

By "nucleic acid library" is meant a collection of isolated DNA or RNA molecules which comprise and substantially represent the entire transcribed fraction of a genome of a specified organism or of a tissue from that organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, 2nd ed., Vol. 1-3 (1989); and *Current Protocols in Molecular Biology*, F. M. Ausubel et al., Eds., Current Protocols, a joint venture between Greene Publishing Associates, Inc. and John Wiley & Sons, Inc. (1994).

As used herein "operably linked" includes reference to a functional linkage of at least two sequences. Operably linked includes linkage between a promoter and a second sequence, wherein the promoter sequence initiates and mediates transcription of the DNA sequence corresponding to the second sequence.

As used herein, "plant" includes plants and plant parts including but not limited to plant cells, plant tissue such as leaves, stems, roots, flowers, and seeds.

As used herein, "polypeptide" means proteins, protein fragments, modified proteins, amino acid sequences and synthetic amino acid sequences. The polypeptide can be glycosylated or not.

As used herein, "promoter" refers to a nucleic acid fragment, e.g., a region of DNA, that is involved in recognition and binding of an RNA polymerase and other proteins to initiate transcription. In other words, this nucleic acid fragment is capable of controlling transcription of another nucleic acid fragment.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 138:267-284 (1984): $T_m=81.5°$ C.$+16.6(\log M)+0.41(\% GC)-0.61(\% form)-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120, or 240 minutes.

The terms "reliable detection" and "reliably detected" are defined herein to mean the reproducible detection of measurable, sequence-specific signal intensity above background noise.

As used herein, "transgenic" refers to a plant or a cell which comprises within its genome a heterologous polynucleotide. Preferably, the heterologous polynucleotide is stably integrated within the genome such that the polynucleotide is passed on, or heritable, to successive generations. The heterologous polynucleotide may be integrated into the genome alone or as part of an expression construct. Transgenic is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" refers to a small nucleic acid molecule (plasmid, virus, bacteriophage, artificial or cut DNA molecule) that can be used to deliver a polynucleotide of the invention into a host cell. Vectors are capable of being replicated and contain cloning sites for introduction of a foreign polynucleotide, Thus, expression vectors permit transcription of a nucleic acid inserted therein.

Polynucleotide sequences may have substantial identity, substantial homology, or substantial complementarity to the selected region of the target gene. As used herein "substantial identity" and "substantial homology" indicate sequences that have sequence identity or homology to each other. Generally, sequences that are substantially identical or substantially homologous will have about 75%, 80%, 85%, 90%, 95%, or 100% sequence identity wherein the percent sequence identity is based on the entire sequence and is determined by GAP alignment using default parameters (GCG, GAP version 10, Accelrys, San Diego, Calif.). GAP uses the algorithm of Needleman and Wunsch (*J. Mol. Biol.* 48:443-453, 1970) to find the alignment of two complete sequences that maximizes the number of matches and minimizes the number of sequence gaps. Sequences which have 100% identity are identical. "Substantial complementarity" refers to sequences that are complementary to each other, and are able to base pair with each other. In describing complementary sequences, if all the nucleotides in the first sequence will base pair to the second sequence, these sequences are fully or completely complementary.

The present invention relates, inter alia, to an isolated polynucleotide comprising: a microRNA selected from the group consisting of SEQ ID NOs:1-2652 and SEQ ID NOs:7959-8114.

In a second embodiment, the invention relates to a full-length complement of the microRNA of selected from the group consisting of SEQ ID NOs:1-2652 and SEQ ID NOs: 7959-8114, or a nucleotide sequence capable of hybridizing to these aforemention microRNAs. wherein the hybridizable nucleotide sequence comprises at least 21 nucleotides.

In a third embodiment, the invention relates to an isolated polynucleotide useful for altering plant gene expression comprising SEQ ID NO:7957 or SEQ ID NO:8427 wherein said isolated polynucleotide comprises at least one functional domain having at least 21(x) contiguous nucleotides and x is an integer from 1 to 2652, further wherein said nucleotides start at nucleotide 1 or any nucleotide 21(x)+1.

In a fourth embodiment, the invention relates to a functional subdomain of such isolated polynucleotides, wherein said functional subdomain comprises at least one microRNA.

In a fifth embodiment, the invention relates to an isolated polynucleotide comprising: a microRNA containing sequence selected from the group consisting of SEQ ID NOs: 5305-7956 and SEQ ID NOs:8271-8426.

Computational identification of miRNAs was accomplished from size selected small RNA libraries from leaf, drought-stressed leaf, seed, and various other tissues.

In some embodiments, the miRNA template, (i.e. the polynucleotide encoding the miRNA), and thereby the miRNA, may comprise some mismatches relative to the target sequence. In some embodiments the miRNA template has ≥1 nucleotide mismatch as compared to the target sequence, for example, the miRNA template can have 1, 2, 3, 4, 5, or more mismatches as compared to the target sequence. This degree of mismatch may also be described by determining the percent identity of the miRNA template to the complement of the target sequence. For example, the miRNA template may have a percent identity including about at least 70%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% as compared to the complement of the target sequence.

In some embodiments, the miRNA template, (i.e. the polynucleotide encoding the miRNA) and thereby the miRNA, may comprise some mismatches relative to the miRNA backside. In some embodiments the miRNA template has ≥1 nucleotide mismatch as compared to the miRNA backside, for example, the miRNA template can have 1, 2, 3, 4, 5, or more mismatches as compared to the miRNA backside. This degree of mismatch may also be described by determining the percent identity of the miRNA template to the complement of the miRNA backside. For example, the miRNA template may have a percent identity including about at least 70%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% as compared to the complement of the miRNA backside.

In some embodiments, the target sequence is selected from a plant pathogen. Plants or cells comprising a miRNA directed to the target sequence of the pathogen are expected to have decreased sensitivity and/or increased resistance to the pathogen. In some embodiments, the miRNA is encoded by a nucleic acid construct further comprising an operably linked promoter. In some embodiments, the promoter is a pathogen-inducible promoter.

In another embodiment, there is provided a nucleic acid construct for suppressing a target sequence. The nucleic acid construct encodes a miRNA substantially complementary to the target. In some embodiments, the nucleic acid construct further comprises a promoter operably linked to the polynucleotide encoding the miRNA. In some embodiments, the nucleic acid construct lacking a promoter is designed and introduced in such a way that it becomes operably linked to a promoter upon integration in the host genome. In some embodiments, the nucleic acid construct is integrated using recombination, including site-specific recombination. See, for example, WO 99/25821, herein incorporated by reference. In some embodiments, the nucleic acid construct is an RNA. In some embodiments, the nucleic acid construct comprises at least one recombination site, including site-specific recombination sites. In some embodiments the nucleic acid construct comprises at least one recombination site in order to facilitate integration, modification, or cloning of the construct. In some embodiments the nucleic acid construct comprises two site-specific recombination sites flanking the miRNA precursor. In some embodiments the site-specific recombination sites include FRT sites, lox sites, or att sites, including attB, attL, attP or attR sites. See, for example, WO 99/25821, and U.S. Pat. Nos. 5,888,732, 6,143,557, 6,171, 861, 6,270,969, and 6,277,608, herein incorporated by reference.

In a sixth embodiment, the invention relates to a DNA expression construct comprising any of the isolated polynucleotides discussed herein operably linked to at least one regulatory sequence.

In a seventh embodiment, the invention relates to a plant comprising in its genome the DNA expression constructs discussed herein. Such plants can be selected from the group consisting of corn, rice, sorghum, sunflower, millet, soybean, canola, wheat, barley, oat, beans, and nuts.

In a eighth embodiment, the invention relates to transgenic seeds obtained from a plant comprising in its genome the DNA expression constructs discussed herein. Also within the scope of the invention are transformed plant tissue or a plant cell comprising in its genome the DNA expression constructs discussed herein.

In an ninth embodiment, the invention relates to by-products and progeny plants obtained from such transgenic seeds.

In another embodiment, the nucleic acid construct comprises an isolated polynucleotide comprising a polynucleotide which encodes a modified plant miRNA precursor, the modified precursor comprising a first and a second oligonucleotide, wherein at least one of the first or the second oligonucleotides is heterologous to the precursor, wherein the first oligonucleotide is substantially complementary to the second oligonucleotide, and the second oligonucleotide comprises a miRNA substantially complementary to the target sequence, wherein the precursor is capable of forming a hairpin.

In some embodiments there are provided cells, plants, and seeds comprising the introduced polynucleotides, and/or produced by the methods of the invention. The cells include prokaryotic and eukaryotic cells, including but not limited to bacteria, yeast, fungi, viral, invertebrate, vertebrate, and plant cells. Plants, plant cells, and seeds of the invention include gynosperms, monocots and dicots, including but not limited to, for example, rice, wheat, oats, barley, millet, sorghum, soy, sunflower, safflower, canola, alfalfa, cotton, *Arabidopsis*, and tobacco.

As used herein, "by-products" refer to any product, fraction, or material produced from the processing of the seed. Corn kernels (seeds) are subjected to both wet and dry milling. The goal of both processes is to separate the germ, the endosperm, and the pericarp (hull). Wet milling separates the chemical constituents of corn into starch, protein, oil, and fiber fractions.

The present invention concerns methods and compositions useful in suppression of a target sequence and/or validation of function. The invention also relates to a method for using microRNA (miRNA) mediated RNA interference (RNAi) to silence or suppress a target sequence to evaluate function, or to validate a target sequence for phenotypic effect and/or trait development. Specifically, the invention relates to constructs comprising small nucleic acid molecules, miRNAs, capable of inducing silencing, and methods of using these miRNAs to selectively silence target sequences.

RNA interference refers to the process of sequence-specific post-transcriptional gene silencing in animals mediated by short interfering RNAs (siRNAs) (Fire et al., *Nature* 391: 806 1998). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., *Trends Genet.* 15:358 1999). Such protection from foreign gene expression may have evolved in response to the production of double-stranded RNAs (dsRNAs) derived from viral infection or from the random integration of transposon elements into a host genome via a cellular response that specifically destroys homologous single-stranded RNA of viral genomic RNA. The presence of dsRNA in cells triggers the RNAi response through a mechanism that has yet to be fully characterized.

The presence of long dsRNAs in cells stimulates the activity of a ribonuclease III enzyme referred to as "dicer". Dicer is involved in the processing of the dsRNA into short pieces of dsRNA known as short interfering RNAs (siRNAs) (Berstein et al., *Nature* 409:363 2001) and/or pre miRNAs into miR-NAs. Short interfering RNAs derived from dicer activity are typically about 21 to about 23 nucleotides in length and comprise about 19 base pair duplexes (Elbashir et al., *Genes Dev.* 15:188 2001). Dicer has also been implicated in the excision of 21- and 22-nucleotide small temporal RNAs (stR-NAs) from precursor RNA of conserved structure that are implicated in translational control (Hutvagner et al., 2001, *Science* 293:834). The RNAi response also features an endonuclease complex, commonly referred to as an RNA-induced silencing complex (RISC), which mediates cleavage of single-stranded RNA having sequence complementarity to the antisense strand of the sRNA duplex. Cleavage of the target RNA takes place in the middle of the region complementary to the antisense strand of the sRNA duplex (Elbashir et al., *Genes Dev.* 15:188 2001). In addition, RNA interference can also involve small RNA (e.g., microRNA, or miRNA) mediated gene silencing, presumably through cellular mechanisms that regulate chromatin structure and thereby prevent transcription of target gene sequences (see, e.g., Allshire, *Science* 297:1818-1819 2002; Volpe et al., *Science* 297:1833-1837 2002; Jenuwein, *Science* 297:2215-2218 2002; and Hall et al., *Science* 297:2232-2237 2002). As such, miRNA molecules of the invention can be used to mediate gene silencing via interaction with RNA transcripts or alternately by interaction with particular gene sequences, wherein such interaction results in gene silencing either at the transcriptional or post-transcriptional level.

RNAi has been studied in a variety of systems. Fire et al. (*Nature* 391:806 1998) were the first to observe RNAi in *C. elegans*. Wianny and Goetz (*Nature Cell Biol.* 2:70 1999) describe RNAi mediated by dsRNA in mouse embryos. Hammond et al. (*Nature* 404:293 2000) describe RNAi in *Drosophila* cells transfected with dsRNA. Elbashir et al., (*Nature* 411:494 2001) describe RNAi induced by introduction of duplexes of synthetic 21-nucleotide RNAs in cultured mammalian cells including human embryonic kidney and HeLa cells.

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

MicroRNAs (miRNAs) are noncoding RNAs of about 19 to about 24 nucleotides (nt) in length that have been identified in both animals and plants (Lagos-Quintana et al., *Science* 294:853-858 2001, Lagos-Quintana et al., *Curr. Biol.* 12:735-739 2002; Lau et al., *Science* 294:858-862 2001; Lee and Ambros, *Science* 294:862-864 2001; Llave et al., *Plant Cell* 14:1605-1619 2002; Mourelatos et al., *Genes. Dev.* 16:720-728 2002; Park et al., *Curr. Biol.* 12:1484-1495 2002; Reinhart et al., *Genes. Dev.* 16:1616-1626 2002). They are processed from longer precursor transcripts that range in size from approximately 70 to 200 nt, and these precursor transcripts have the ability to form stable hairpin structures. In animals, the enzyme involved in processing miRNA precursors is called Dicer, an RNAse III-like protein (Grishok et al., *Cell* 106:23-34 2001; Hutvagner et al., *Science* 293:834-838 2001; Ketting et al., *Genes. Dev.* 15:2654-2659 2001). Plants also have a Dicer-like enzyme, DCL1 (previously named CARPEL FACTORY/SHORT INTEGUMENTS1/SUS-PENSOR1), and recent evidence indicates that it, like Dicer, is involved in processing the hairpin precursors to generate mature miRNAs (Park et al., *Curr. Biol.* 12:1484-1495 2002; Reinhart et al., *Genes. Dev.* 16:1616-1626 2002). Furthermore, it is becoming clear from recent work that at least some miRNA hairpin precursors originate as longer polyadenylated transcripts, and several different miRNAs and associated hairpins can be present in a single transcript (Lagos-Quintana et al., *Science* 294:853-858 2001; Lee et al., *EMBO J* 21:4663-4670 2002). Recent work has also examined the selection of the miRNA strand from the dsRNA product arising from processing of the hairpin by DICER (Schwartz et al., 2003, *Cell* 115:199-208). It appears that the stability (i.e. G:C vs. A:U content, and/or mismatches) of the two ends of the processed dsRNA affects the strand selection, with the low stability end being easier to unwind by a helicase activity. The 5' end strand at the low stability end is incorporated into the RISC complex, while the other strand is degraded.

In animals, there is direct evidence indicating a role for specific miRNAs in development. The lin-4 and let-7 miR-NAs in *C. elegans* have been found to control temporal development, based on the phenotypes generated when the genes producing the lin-4 and let-7 miRNAs are mutated (Lee et al., *Cell* 75:843-854 1993; Reinhart et al., *Nature* 403-901-906 2000). In addition, both miRNAs display a temporal expression pattern consistent with their roles in developmental timing. Other animal miRNAs display developmentally regulated patterns of expression, both temporal and tissue-specific (Lagos-Quintana et al., *Science* 294:853-853 2001, Lagos-Quintana et al., *Curr. Biol.* 12:735-739 2002; Lau et al., *Science* 294:858-862 2001; Lee and Ambros, *Science* 294: 862-864 2001), leading to the hypothesis that miRNAs may, in many cases, be involved in the regulation of important developmental processes. Likewise, in plants, the differential expression patterns of many miRNAs suggests a role in development (Llave et al., *Plant Cell* 14:1605-1619 2002; Park et al., *Curr. Biol.* 12:1484-1495 2002; Reinhart et al., *Genes. Dev.* 16:1616-1626 2002). However, a developmental role for miRNAs has not been directly proven in plants, because to date there has been no report of a developmental phenotype associated with a specific plant miRNA.

MicroRNAs appear to regulate target genes by binding to complementary sequences located in the transcripts produced by these genes. In the case of lin-4 and let-7, the target sites are located in the 3' UTRs of the target mRNAs (Lee et al., *Cell* 75:843-854 1993; Wightman et al., *Cell* 75:855-862 1993; Reinhart et al., *Nature* 403:901-906 2000; Slack et al., *Mol. Cell* 5:659-669 2000), and there are several mismatches between the lin-4 and let-7 miRNAs and their target sites. Binding of the lin-4 or let-7 miRNA appears to cause downregulation of steady-state levels of the protein encoded by the target mRNA without affecting the transcript itself (Olsen and Ambros, *Dev. Biol.* 216:671-680 1999). On the other hand, recent evidence suggests that miRNAs can, in some cases, cause specific RNA cleavage of the target transcript within the target site, and this cleavage step appears to require 100% complementarity between the miRNA and the target transcript (Hutvagner and Zamore, *Science* 297:2056-2060 2002; Llave et al., *Plant Cell* 14:1605-1619 2002). It seems likely that miRNAs can enter at least two pathways of target gene regulation: Protein downregulation when target complementarity is <100%, and RNA cleavage when target complementarity is 100%. MicroRNAs entering the RNA cleavage pathway are analogous to the 21-25 nt short interfering RNAs (siRNAs) generated during RNA interference (RNAi) in animals and posttranscriptional gene silencing (PTGS) in plants (Hamilton and Baulcombe 1999; Hammond et al., 2000; Zamore et al., 2000; Elbashir et al., 2001), and likely are incorporated into an RNA-induced silencing complex (RISC) that is similar or identical to that seen for RNAi.

Identifying the targets of miRNAs with bioinformatics has not been successful in animals, and this is probably due to the fact that animal miRNAs have a low degree of complementarity with their targets. On the other hand, bioinformatic approaches have been successfully used to predict targets for plant miRNAs (Llave et al., *Plant Cell* 14:1605-1619 2002; Park et al., *Curr. Biol.* 12:1484-1495 2002; Rhoades et al., *Cell* 110:513-520 2002), and thus it appears that plant miRNAs have higher overall complementarity with their putative targets than do animal miRNAs. Most of these predicted target transcripts of plant miRNAs encode members of transcription factor families implicated in plant developmental patterning or cell differentiation. Nonetheless, biological function has not been directly demonstrated for any plant miRNA. Although Llave et al. (*Science* 297:2053-2056 2002) have shown that a transcript for a SCARECROW-like transcription factor is a target of the *Arabidopsis* miRNA mir171, these studies were performed in a heterologous species and no plant phenotype associated with mir171 was reported.

The methods provided can be practiced in any organism in which a method of transformation is available, and for which there is at least some sequence information for the target sequence, or for a region flanking the target sequence of interest. It is also understood that two or more sequences could be targeted by sequential transformation, co-transformation with more than one targeting vector, or the construction of a DNA construct comprising more than one miRNA sequence. The methods of the invention may also be implemented by a combinatorial nucleic acid library construction in order to generate a library of miRNAs directed to random target sequences. The library of miRNAs could be used for high-throughput screening for gene function validation.

General categories of sequences of interest include, for example, those genes involved in regulation or information, such as zinc fingers, transcription factors, homeotic genes, or cell cycle and cell death modulators, those involved in communication, such as kinases, and those involved in housekeeping, such as heat shock proteins.

Target sequences further include coding regions and noncoding regions such as promoters, enhancers, terminators, introns and the like, which may be modified in order to alter the expression of a gene of interest. For example, an intron sequence can be added to the 5' region to increase the amount of mature message that accumulates (see for example Buchman and Berg, *Mol. Cell Biol.* 8:4395-4405 (1988); and Callis et al., *Genes Dev.* 1:1183-1200 (1987)).

The target sequence may be an endogenous sequence, or may be an introduced heterologous sequence, or transgene. For example, the methods may be used to alter the regulation or expression of a transgene, or to remove a transgene or other introduced sequence such as an introduced site-specific recombination site. The target sequence may also be a sequence from a pathogen, for example, the target sequence may be from a plant pathogen such as a virus, a mold or fungus, an insect, or a nematode. A miRNA could be expressed in a plant which, upon infection or infestation, would target the pathogen and confer some degree of resistance to the plant.

In plants, other categories of target sequences include genes affecting agronomic traits, insect resistance, disease resistance, herbicide resistance, sterility, grain characteristics, and commercial products. Genes of interest also included those involved in oil, starch, carbohydrate, or nutrient metabolism as well as those affecting, for example, kernel size, sucrose loading, and the like. The quality of grain is reflected in traits such as levels and types of oils, saturated and unsaturated, quality and quantity of essential amino acids, and levels of cellulose. For example, genes of the phytic acid biosynthetic pathway could be suppressed to generate a high available phosphorous phenotype. See, for example, phytic acid biosynthetic enzymes including inositol polyphosphate kinase-2 polynucleotides, disclosed in WO 02/059324, inositol 1,3,4-trisphosphate 5/6-kinase polynucleotides, disclosed in WO 03/027243, and myo-inositol 1-phosphate synthase and other phytate biosynthetic polynucleotides, disclosed in WO 99/05298, all of which are herein incorporated by reference. Genes in the lignification pathway could be suppressed to enhance digestibility or energy availability. Genes affecting cell cycle or cell death could be suppressed to affect growth or stress response. Genes affecting DNA repair and/or recombination could be suppressed to increase genetic variability. Genes affecting flowering time could be suppressed, as well as genes affecting fertility. Any target sequence could be suppressed in order to evaluate or confirm its role in a particular trait or phenotype, or to dissect a molecular, regulatory, biochemical, or proteomic pathway or network.

A number of promoters can be used, these promoters can be selected based on the desired outcome. It is recognized that different applications will be enhanced by the use of different promoters in plant expression cassettes to modulate the timing, location and/or level of expression of the miRNA. Such plant expression cassettes may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

Constitutive, tissue-preferred or inducible promoters can be employed. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter and other transcription initiation regions from various plant genes known to those of skill. If low level expression is desired, weak promoter(s) may be used. Weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608, 144; 5,604,121; 5,569,597; 5,466,785; 5,399,680; 5,268,463; and 5,608,142. See also, U.S. Pat. No. 6,177,611, herein incorporated by reference.

Examples of inducible promoters are the Adh1 promoter which is inducible by hypoxia or cold stress, the Hsp70 promoter which is inducible by heat stress, the PPDK promoter and the pepcarboxylase promoter which are both inducible by light. Also useful are promoters which are chemically inducible, such as the In2-2 promoter which is safener induced (U.S. Pat. No. 5,364,780), the ERE promoter which is estrogen induced, and the Axig1 promoter which is auxin induced and tapetum specific but also active in callus (PCT US01/22169).

Examples of promoters under developmental control include promoters that initiate transcription preferentially in certain tissues, such as leaves, roots, fruit, seeds, or flowers. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promoter, Boronat, A. et al. (1986) *Plant Sci.* 47:95-102; Reina, M. et al. *Nucl. Acids Res.* 18(21):6426; and Kloesgen, R. B. et al. (1986) *Mol. Gen. Genet.* 203:237-244. Promoters that express in the embryo, pericarp, and endosperm are disclosed in U.S. Pat. No. 6,225, 529 and PCT publication WO 00/12733. The disclosures each of these are incorporated herein by reference in their entirety.

In some embodiments it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant. Path.* 41:189-200).

Additionally, as pathogens find entry into plants through wounds or insect damage, a wound-inducible promoter may be used in the constructions of the polynucleotides. Such wound-inducible promoters include potato proteinase inhibitor (pin II) gene (Ryan (1990) *Ann. Rev. Phytopath.* 28:425-449; Duan et al. (1996) *Nature Biotech.* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Lett.* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression of a sequence of interest within a particular plant tissue. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen. Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590. In addition, the promoters of cab and rubisco can also be used. See, for example, Simpson et al. (1958) *EMBO J* 4:2723-2729 and Timko et al. (1988) *Nature* 318:57-58.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed roIC and roID root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and roIB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179. The phaseolin gene (Murai et al. (1983) *Science* 23:476-482 and Sengopta-Gopalen et al. (1988) *PNAS* 82:3320-3324.

Transformation protocols as well as protocols for introducing nucleotide sequences into plants may vary depending on the type of plant or plant cell, i.e., monocot or dicot, targeted for transformation. Suitable methods of introducing the DNA construct include microinjection (Crossway et al. (1986) *Biotechniques* 4:320-334; and U.S. Pat. No. 6,300,543), sexual crossing, electroporation (Riggs et al. (1986) *Proc. Natl. Acad. Sci. USA* 83:5602-5606), *Agrobacterium*-mediated transformation (Townsend et al., U.S. Pat. No. 5,563,055; and U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923-926). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); and U.S. Pat. No. 5,736,369 (meristem transformation), all of which are herein incorporated by reference.

The nucleotide constructs may be introduced into plants by contacting plants with a virus or viral nucleic acids. Generally, such methods involve incorporating a nucleotide construct of the invention within a viral DNA or RNA molecule. Further, it is recognized that useful promoters encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

In some embodiments, transient expression may be desired. In those cases, standard transient transformation techniques may be used. Such methods include, but are not limited to viral transformation methods, and microinjection of DNA or RNA, as well other methods well known in the art.

The cells from the plants that have stably incorporated the nucleotide sequence may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic imparted by the nucleotide sequence of interest and/or the genetic markers contained within the target site or transfer cassette. Two or more generations may be grown to ensure that expression of the desired phenotypic characteristic is stably maintained and inherited and then seeds harvested to ensure expression of the desired phenotypic characteristic has been achieved.

In a tenth embodiment, the invention relates to a method for altering expression of a stably introduced nucleotide sequence in a plant comprising:

a) making a DNA expression construct comprising a stably introduced nucleotide sequence and at least one sequence capable of hybridizing to the isolated polynucleotide of the invention;
  b) transforming a plant with the DNA expression construct of part (a); and c) selecting a transformed plant which comprises the DNA expression construct of part (a) in its genome and which has altered expression of the stably introduced nucleotide sequence when compared to a plant transformed with a modified version of the DNA expression construct of part (a) wherein the modified construct lacks the sequence capable of hybridizing to the isolated polynucleotide of the invention.

Initial identification and selection of cells and/or plants comprising the DNA constructs may be facilitated by the use of marker genes. Gene targeting can be performed without selection if there is a sensitive method for identifying recombinants, for example if the targeted gene modification can be easily detected by PCR analysis, or if it results in a certain phenotype. However, in most cases, identification of gene targeting events will be facilitated by the use of markers. Useful markers include positive and negative selectable markers as well as markers that facilitate screening, such as visual markers. Selectable markers include genes carrying resistance to an antibiotic such as spectinomycin (e.g. the aada gene, Svab et al. 1990 *Plant Mol. Biol.* 14:197), streptomycin (e.g., aada, or SPT, Svab et al. 1990 *Plant Mol. Biol.* 14:197; Jones et al. 1987 *Mol. Gen. Genet.* 210:86), kanamycin (e.g., nptII, Fraley et al. 1983 *PNAS* 80:4803), hygromycin (e.g., HPT, Vanden Elzen et al. 1985 *Plant Mol. Biol.* 5:299), gentamycin (Hayford et al. 1988 *Plant Physiol.* 86:1216), phleomycin, zeocin, or bleomycin (Hille et al. 1986 *Plant Mol. Biol.* 7:171), or resistance to a herbicide such as phosphinothricin (bar gene), or sulfonylurea (acetolactate synthase (ALS)) (Charest et al. (1990) *Plant Cell Rep.* 8:643), genes that fulfill a growth requirement on an incomplete media such as HIS3, LEU2, URA3, LYS2, and TRP1 genes in yeast, and other such genes known in the art. Negative selectable markers include cytosine deaminase (codA) (Stougaard 1993 *Plant J.* 3:755-761), tms2 (DePicker et al. 1988 *Plant Cell Rep.* 7:63-66), nitrate reductase (Nussame et al. 1991 *Plant J.* 1:267-274), SU1 (O'Keefe et al. 1994 *Plant Physiol.* 105:473-482), aux-2 from the Ti plasmid of *Agrobacterium*, and thymidine kinase. Screenable markers include fluorescent proteins such as green fluorescent protein (GFP) (Chalfie et al., 1994 *Science* 263:802; U.S. Pat. No. 6,146,826; U.S. Pat. No. 5,491,084; and WO 97/41228), reporter enzymes such as β-glucuronidase (GUS) (Jefferson R. A. 1987 *Plant Mol. Biol. Rep.* 5:387; U.S. Pat. No. 5,599,670; and U.S. Pat. No. 5,432,081), β-galactosidase (lacZ), alkaline phosphatase (AP), glutathione S-transferase (GST) and luciferase (U.S. Pat. No. 5,674,713; and Ow et al. 1986 *Science* 234(4778): 856-859), visual markers like anthocyanins such as CRC (Ludwig et al. (1990) *Science* 247(4841):449-450) R gene family (e.g. Lc, P, S), A, C, R-nj, body and/or eye color genes in *Drosophila*, coat color genes in mammalian systems, and others known in the art.

One or more markers may be used in order to select and screen for gene targeting events. One common strategy for gene disruption involves using a target modifying polynucleotide in which the target is disrupted by a promoterless selectable marker. Since the selectable marker lacks a promoter, random integration events are unlikely to lead to transcription of the gene. Gene targeting events will put the selectable marker under control of the promoter for the target gene. Gene targeting events are identified by selection for expression of the selectable marker. Another common strategy utilizes a positive-negative selection scheme. This scheme utilizes two selectable markers, one that confers resistance (R+) coupled with one that confers a sensitivity (S+), each with a promoter. When this polynucleotide is randomly inserted, the resulting phenotype is R+/S+. When a gene targeting event is generated, the two markers are uncoupled and the resulting phenotype is R+/S−. Examples of using positive-negative selection are found in Thykjr et al. (1997) *Plant Mol. Biol.* 35:523-530; and WO 01/66717, which are herein incorporated by reference.

EXAMPLES

The following are non-limiting examples intended to illustrate the invention. Although the present invention has been described in some detail by way of illustration and example for purposes of clarity of understanding, it will be obvious that certain changes and modifications may be practiced within the scope of the appended claims.

Example 1

Transformation of Plants

Described in this example are methods one may use for introduction of a polynucleotide or polypeptide into a plant cell.

A. Maize Particle-Mediated DNA Delivery

A DNA construct can be introduced into maize cells capable of growth on suitable maize culture medium. Such competent cells can be from maize suspension culture, callus culture on solid medium, freshly isolated immature embryos or meristem cells. Immature embryos of the Hi-II genotype can be used as the target cells. Ears are harvested at approximately 10 days post-pollination, and 1.2-1.5 mm immature embryos are isolated from the kernels, and placed scutellum-side down on maize culture medium.

The immature embryos are bombarded from 18-72 hours after being harvested from the ear. Between 6 and 18 hours prior to bombardment, the immature embryos are placed on medium with additional osmoticum (MS basal medium, Musashige and Skoog, 1962, *Physiol. Plant* 15:473-497, with 0.25 M sorbitol). The embryos on the high-osmotic medium are used as the bombardment target, and are left on this medium for an additional 18 hours after bombardment.

For particle bombardment, plasmid DNA (described above) is precipitated onto 1.8 mm tungsten particles using standard CaCl2-spermidine chemistry (see, for example, Klein et al., 1987, *Nature* 327:70-73). Each plate is bombarded once at 600 PSI, using a DuPont Helium Gun (Lowe et al., 1995, *Bio/Technol* 13:677-682). For typical media formulations used for maize immature embryo isolation, callus initiation, callus proliferation and regeneration of plants, see Armstrong, C., 1994, In "The Maize Handbook", M. Freeling and V. Walbot, eds. Springer Verlag, N.Y., pp 663-671.

Within 1-7 days after particle bombardment, the embryos are moved onto N6-based culture medium containing 3 mg/l of the selective agent bialaphos. Embryos, and later callus, are transferred to fresh selection plates every 2 weeks. The calli developing from the immature embryos are screened for the desired phenotype. After 6-8 weeks, transformed calli are recovered.

B. Soybean Transformation

Soybean embryogenic suspension cultures are maintained in 35 ml liquid media SB196 or SB172 in 250 ml Erlenmeyer flasks on a rotary shaker, 150 rpm, 26 C with cool white fluorescent lights on 16:8 hr day/night photoperiod at light intensity of 30-35 uE/m2s. Cultures are subcultured every two weeks by inoculating approximately 35 mg of tissue into 35 ml of fresh liquid media. Alternatively, cultures are initiated and maintained in 6-well Costar plates.

SB 172 media is prepared as follows: (per liter), 1 bottle Murashige and Skoog Medium (Duchefa #M 0240), 1 ml B5 vitamins 1000× stock, 1 ml 2,4-D stock (Gibco 11215-019), 60 g sucrose, 2 g MES, 0.667 g L-Asparagine anhydrous (GibcoBRL 11013-026), pH 5.7. SB 196 media is prepared as follows: (per liter) 10 ml MS FeEDTA, 10 ml MS Sulfate, 10 ml FN-Lite Halides, 10 ml FN-Lite P,B,Mo, 1 ml B5 vitamins 1000× stock, 1 ml 2,4-D, (Gibco 11215-019), 2.83 g KNO3, 0.463 g (NH4)2SO4, 2 g MES, 1 g Asparagine Anhydrous, Powder (Gibco 11013-026), 10 g Sucrose, pH 5.8. 2,4-D stock concentration 10 mg/ml is prepared as follows: 2,4-D is solubilized in 0.1 N NaOH, filter-sterilized, and stored at −20° C. B5 vitamins 1000× stock is prepared as follows: (per 100 ml)-store aliquots at −20° C., 10 g myo-inositol, 100 mg nicotinic acid, 100 mg pyridoxine HCl, 1 g thiamin.

Soybean embryogenic suspension cultures are transformed with various plasmids by the method of particle gun bombardment (Klein et al., 1987 *Nature* 327:70. To prepare tissue for bombardment, approximately two flasks of suspension culture tissue that has had approximately 1 to 2 weeks to recover since its most recent subculture is placed in a sterile 60×20 mm petri dish containing 1 sterile filter paper in the bottom to help absorb moisture. Tissue (i.e. suspension clusters approximately 3-5 mm in size) is spread evenly across each petri plate. Residual liquid is removed from the tissue with a pipette, or allowed to evaporate to remove excess moisture prior to bombardment. Per experiment, 4-6 plates of tissue are bombarded. Each plate is made from two flasks.

To prepare gold particles for bombardment, 30 mg gold is washed in ethanol, centrifuged and resuspended in 0.5 ml of sterile water. For each plasmid combination (treatments) to be used for bombardment, a separate micro-centrifuge tube is prepared, starting with 50 μl of the gold particles prepared above. Into each tube, the following are also added; 5 μl of plasmid DNA (at 1 μg/μl), 50 μl CaCl2, and 20 μl 0.1 M spermidine. This mixture is agitated on a vortex shaker for 3 minutes, and then centrifuged using a microcentrifuge set at 14,000 RPM for 10 seconds. The supernatant is decanted and the gold particles with attached, precipitated DNA are washed twice with 400 μl aliquots of ethanol (with a brief centrifugation as above between each washing). The final volume of 100% ethanol per each tube is adjusted to 40 μl, and this particle/DNA suspension is kept on ice until being used for bombardment.

Immediately before applying the particle/DNA suspension, the tube is briefly dipped into a sonicator bath to disperse the particles, and then 5 μL of DNA prep is pipetted onto each flying disk and allowed to dry. The flying disk is then placed into the DuPont Biolistics PDS1000/HE. Using the DuPont Biolistic PDS1000/HE instrument for particle-mediated DNA delivery into soybean suspension clusters, the following settings are used. The membrane rupture pressure is 1100 psi. The chamber is evacuated to a vacuum of 27-28 inches of mercury. The tissue is placed approximately 3.5 inches from the retaining/stopping screen (3rd shelf from the bottom). Each plate is bombarded twice, and the tissue clusters are rearranged using a sterile spatula between shots.

Following bombardment, the tissue is re-suspended in liquid culture medium, each plate being divided between 2 flasks with fresh SB196 or SB172 media and cultured as described above. Four to seven days post-bombardment, the medium is replaced with fresh medium containing a selection agent. The selection media is refreshed weekly for 4 weeks and once again at 6 weeks. Weekly replacement after 4 weeks may be necessary if cell density and media turbidity is high.

Four to eight weeks post-bombardment, green, transformed tissue may be observed growing from untransformed, necrotic embryogenic clusters. Isolated, green tissue is removed and inoculated into 6-well microtiter plates with liquid medium to generate clonally-propagated, transformed embryogenic suspension cultures.

Each embryogenic cluster is placed into one well of a Costar 6-well plate with 5 mls fresh SB196 media with selection agent. Cultures are maintained for 2-6 weeks with fresh media changes every 2 weeks. When enough tissue is available, a portion of surviving transformed clones are subcultured to a second 6-well plate as a back-up to protect against contamination.

To promote in vitro maturation, transformed embryogenic clusters are removed from liquid SB196 and placed on solid agar media, SB 166, for 2 weeks. Tissue clumps of 2-4 mm size are plated at a tissue density of 10 to 15 clusters per plate. Plates are incubated in diffuse, low light (<10 μE) at 26+/−1° C. After two weeks, clusters are subcultured to SB 103 media for 3-4 weeks.

SB 166 is prepared as follows: (per liter), 1 pkg. MS salts (Gibco/BRL—Cat #11117-017), 1 ml B5 vitamins 1000× stock, 60 g maltose, 750 mg MgCl2 hexahydrate, 5 g activated charcoal, pH 5.7, 2 g gelrite. SB 103 media is prepared as follows: (per liter), 1 pkg. MS salts (Gibco/BRL—Cat #11117-017), 1 ml B5 vitamins 1000× stock, 60 g maltose, 750 mg MgCl2 hexahydrate, pH 5.7, 2 g gelrite. After 5-6 week maturation, individual embryos are desiccated by placing embryos into a 100×15 petri dish with a 1 cm2 portion of the SB103 media to create a chamber with enough humidity to promote partial desiccation, but not death.

Approximately 25 embryos are desiccated per plate. Plates are sealed with several layers of parafilm and again are placed in a lower light condition. The duration of the desiccation step is best determined empirically, and depends on size and quantity of embryos placed per plate. For example, small embryos or few embryos/plate require a shorter drying period, while large embryos or many embryos/plate require a longer drying period. It is best to check on the embryos after about 3 days, but proper desiccation will most likely take 5 to 7 days. Embryos will decrease in size during this process.

Desiccated embryos are planted in SB 71-1 or MSO medium where they are left to germinate under the same culture conditions described for the suspension cultures. When the plantlets have two fully-expanded trifoliate leaves, germinated and rooted embryos are transferred to sterile soil and watered with MS fertilizer. Plants are grown to maturity for seed collection and analysis. Healthy, fertile transgenic plants are grown in the greenhouse.

SB 71-1 is prepared as follows: 1 bottle Gamborg's B5 salts w/sucrose (Gibco/BRL—Cat #21153-036), 10 g sucrose, 750 mg MgCl2 hexahydrate, pH 5.7, 2 g gelrite. MSO media is prepared as follows: 1 pkg Murashige and Skoog salts (Gibco 11117-066), 1 ml B5 vitamins 1000× stock, 30 g sucrose, pH 5.8, 2 g Gelrite.

C. Transformation of Maize Using *Agrobacterium*

*Agrobacterium*-mediated transformation of maize is performed essentially as described by Zhao et al., in *Meth. Mol. Biol.* 318:315-323 (2006) (see also Zhao et al., *Mol. Breed.* 8:323-333 (2001) and U.S. Pat. No. 5,981,840 issued Nov. 9, 1999, incorporated herein by reference). The transformation process involves bacterium inoculation, co-cultivation, resting, selection and plant regeneration.

1. Immature Embryo Preparation:

Immature maize embryos are dissected from caryopses and placed in a 2 mL microtube containing 2 mL PHI-A medium.

2. *Agrobacterium* Infection and Co-Cultivation of Immature Embryos:

2.1 Infection Step:

PHI-A medium of (1) is removed with 1 mL micropipettor, and 1 mL of *Agrobacterium* suspension is added. The tube is gently inverted to mix. The mixture is incubated for 5 min at room temperature.

2.2 Co-Culture Step:

The *Agrobacterium* suspension is removed from the infection step with a 1 mL micropipettor. Using a sterile spatula the embryos are scraped from the tube and transferred to a plate of PHI-B medium in a 100×15 mm Petri dish. The embryos are oriented with the embryonic axis down on the surface of the medium. Plates with the embryos are cultured at 20° C., in darkness, for three days. L-Cysteine can be used in the co-cultivation phase. With the standard binary vector, the co-cultivation medium supplied with 100-400 mg/L L-cysteine is critical for recovering stable transgenic events.

3. Selection of Putative Transgenic Events:

To each plate of PHI-D medium in a 100×15 mm Petri dish, 10 embryos are transferred, maintaining orientation and the dishes are sealed with parafilm. The plates are incubated in darkness at 28° C. Actively growing putative events, as pale yellow embryonic tissue, are expected to be visible in six to eight weeks. Embryos that produce no events may be brown and necrotic, and little friable tissue growth is evident. Putative transgenic embryonic tissue is subcultured to fresh PHI-D plates at two-three week intervals, depending on growth rate. The events are recorded.

4. Regeneration of T0 Plants:

Embryonic tissue propagated on PHI-D medium is subcultured to PHI-E medium (somatic embryo maturation medium), in 100×25 mm Petri dishes and incubated at 28° C., in darkness, until somatic embryos mature, for about ten to eighteen days. Individual, matured somatic embryos with well-defined scutellum and coleoptile are transferred to PHI-F embryo germination medium and incubated at 28° C. in the light (about 80 µE from cool white or equivalent fluorescent lamps). In seven to ten days, regenerated plants, about 10 cm tall, are potted in horticultural mix and hardened-off using standard horticultural methods.

Media for Plant Transformation:

1. PHI-A: 4 g/L CHU basal salts, 1.0 mL/L 1000× Eriksson's vitamin mix, 0.5 mg/L thiamin HCl, 1.5 mg/L 2,4-D, 0.69 g/L L-proline, 68.5 g/L sucrose, 36 g/L glucose, pH 5.2. Add 100 µM acetosyringone (filter-sterilized).
2. PHI-B: PHI-A without glucose, increase 2,4-D to 2 mg/L, reduce sucrose to 30 g/L and supplemented with 0.85 mg/L silver nitrate (filter-sterilized), 3.0 g/L Gelrite®, 100 µM acetosyringone (filter-sterilized), pH 5.8.
3. PHI-C: PHI-B without Gelrite® and acetosyringonee, reduce 2,4-D to 1.5 mg/L and supplemented with 8.0 g/L agar, 0.5 g/L 2-[N-morpholino]ethane-sulfonic acid (MES) buffer, 100 mg/L carbenicillin (filter-sterilized).
4. PHI-D: PHI-C supplemented with 3 mg/L bialaphos (filter-sterilized).
5. PHI-E: 4.3 g/L of Murashige and Skoog (MS) salts, (Gibco, BRL 11117-074), 0.5 mg/L nicotinic acid, 0.1 mg/L thiamine HCl, 0.5 mg/L pyridoxine HCl, 2.0 mg/L glycine, 0.1 g/L myo-inositol, 0.5 mg/L zeatin (Sigma, Cat. No. Z-0164), 1 mg/L indole acetic acid (IAA), 26.4 µg/L abscisic acid (ABA), 60 g/L sucrose, 3 mg/L bialaphos (filter-sterilized), 100 mg/L carbenicillin (filter-sterilized), 8 g/L agar, pH 5.6.
6. PHI-F: PHI-E without zeatin, IAA, ABA; reduce sucrose to 40 g/L; replacing agar with 1.5 g/L Gelrite®; pH 5.6.

Plants can be regenerated from the transgenic callus by first transferring clusters of tissue to N6 medium supplemented with 0.2 mg per liter of 2,4-D. After two weeks the tissue can be transferred to regeneration medium (Fromm et al., *Bio/Technology* 8:833-839 (1990)).

Transgenic T0 plants can be regenerated and their phenotype determined. T1 seed can be collected.

Furthermore, a recombinant DNA construct containing a validated *Arabidopsis* gene can be introduced into a maize inbred line either by direct transformation or introgression from a separately transformed line.

Transgenic plants, either inbred or hybrid, can undergo more vigorous field-based experiments to study expression effects.

Example 2

Isolation of Small RNAs for MPSS or 454 Sequencing

RNA samples were extracted using Trizol reagent (Invitrogen), from the following tissues: drought-stressed maize leaves, well-watered maize leaves, unfertilized maize ovules, early stage maize kernels (2 days after pollination), mixed later stages maize kernels (7, 14 and 21 days after pollination). Total RNA was fractionated on 15% polyacrylamide TBE/urea gels, and a 21-nt RNA marker was also included in a separate lane. Following electrophoresis, the gels were stained with ethidium bromide, and the region of the gel corresponding to 20-22 nucleotides was excised. The small RNA fraction was eluted overnight, ethanol precipitated, and then ligated sequentially to 5' and 3' RNA adaptors, using T4 RNA ligase (5' RNA adaptor GGUCUUAGUCGCAUCCU-GUAGAUGGAUC and 3' RNA adaptor pAUGCA-CACUGAUGCUGACACCUGCidT where p=phosphate; idT=inverted deoxythymidine; SEQ ID NOs:8428 and 8429, respectively). The products of each ligation were gel purified on 10% denaturing polyacrylamide gels, to remove unligated adaptors. RT-PCR was then carried out on the final ligation product, using primers complementary to the 5' and 3' adaptor sequences. Amplified cDNAs corresponding to small RNAs were sequenced using one of three methods: concatamerization followed by standard dideoxy sequencing (Elbashir et al., 2001 *Genes & Dev.* 15: 188-200), Massively Parallel Signature Sequencing (MPSS™) tag sequencing (Solexa) or 454™ sequencing (454 Life Sciences), or small RNA sequencing by SBS (Sequencing-By-Synthesis; Illumina™ Inc. San Diego, Calif.).

Example 3

Identification of Maize miRNA Sequences

Experimental data are analyzed by a program called "mirna", referred to as "the program". The program is written in the Perl programming language. It runs mainly from a CGI web interface, but also can be run from the command line.

For any particular combination of *Zea mays* genomic data and experimental results, experimental sequence data from MPSS or 454 sequencing is located in a maize genomic database; those which show a match between experimental sequence and genomic sequences are called "tags". A mixture of proprietary and public genomic data are assembled into a set of contigs. Any non-contiguous genomic sequence or unassembled genomic sequence is searched separately. In addition, data derived from B73 and MO17 cultivars are kept separate. All subsequent analysis is performed only on tags identified by matching sequences from the small RNA MPSS or 454 experiments to sequences located in the genomic databases.

A selectable series of screens is applied to these tags to determine computationally which tags are likely to represent miRNAs. Each screen can be selected or skipped by the user running the analysis. The screens include: removing tags found in repeat regions; removing tags that match known RNA; combining tags that have significant overlap in the genomic data; removing tags that match published known miRNAs; removing tags that appear near each other in clusters; removing tags that have a low PPM (parts-per-million, a measure of frequency) value in the experimental data; removing tags that do not have an easily identifiable base-pairing sequence nearby in the genome; and testing the region of the genome surrounding the tag for good RNA folding characteristics.

The RNA folding tests are performed by first employing a publicly available RNA folding algorithm (Vienna RNA Package) on a 500 bp region of the genome containing the tag. Regions that do not fold according to the default parameters (including a Gibbs free energy of −30 ΔG; Hofacker et al. 1994 Monatsh. Chem. 125: 167-188) are removed from further consideration. A selectable series of tests are employed with adjustable parameters to identify those tags whose folds appear to be miRNA precursors. These parameters include several restrictions on the size and number of mismatched basepairs in the putative fold; the size and conformation of the hairpin region of the fold; matching characteristics of certain bases commonly found in miRNAs; and the folding characteristics of the region adjacent to the miRNA precursor.

The set of tags which pass these computational screens are then examined in several graphic displays that represent the fold, the putative miRNA, and the detailed results of the folding tests and other experimental results. This examination may result in a tag being rejected by an expert that had passed the computational screens. Additional computational screens that are suggested by these expert examinations may then be incorporated into the program.

The biological validity of the miRNA sequences is further tested by using WU-BLAST (Gish, Washington University at St. Louis; Altschul et al 1990 *J Mol Biol* 215:403-410) analysis to identify the putative genomic targets. Given the incomplete nature of the maize genome tags are not rejected on the basis of this target examination. However, computational identification of a target increases the likelihood that the miRNA sequence is biologically active. A combination of rice and maize genomic data are used in the identification of putative targets.

Example 4

Maize miRNA Sequences

The protocol outlined in Example 3 was employed on maize RNA isolated from the following maize tissues: drought-stressed maize leaves, well-watered maize leaves, unfertilized maize ovules, early stage maize kernels (2 days after pollination), mixed later stages maize kernels (7, 14 and 21 days after pollination).

Analysis yielded 2808 maize microRNA sequences (see Table 1 showing SEQ ID NOs:1-2652 found in U.S. Provisional Application No. 60/849,672, filed Oct. 5, 2006, and 156 additional microRNA sequences added herein SEQ ID NOs:7959-8114).

Known miRNA sequences were excluded from this list. Many of the known miRNA sequences were found to be abundantly represented in the sequenced libraries and were identified by the protocol outlined in this application. Known miRNA sequences were not limited to maize, even though the starting RNAs were all from maize. Therefore, it is expected that the 2808 miRNA sequences from maize disclosed in this application is a population enriched for maize-specific and lower abundance miRNA species. It should be noted that "lower abundance" is a relative term and the absolute amount of any given microRNA sequence in any given tissue or developmental state may be widely variable.

Example 5

Expression Analysis of Maize miRNAs

Expression analysis can be used to provide further evidence that a given small RNA sequence corresponds to a miRNA. The ability to detect a miRNA by Northern blotting and hybridization is a standard criterion used by researchers to validate candidate miRNAs (Ambros et al., 2003). Alternatively, RT-PCR protocols have been developed that allow detection of small RNAs that are of lower abundance (Shi and Chiang, 2005; Chen et al., 2005). We will use one or both of these procedures to validate selected candidate miRNAs from our list. In addition, most if not all of the miRNA candidates we are disclosing will be included as features on a microarray chip, which will allow hybridization to small RNA fractions of a variety of tissues and treatments. Expression profiling of miRNAs by microarray analysis is a rapidly evolving and robust technology that should allow further validation of candidate miRNAs, as well as provide information on tissue specificity and/or conditional expression of particular miRNAs.

Particular miRNA candidates may have clearly recognizable target transcripts based on bioinformatic analysis, which provides an opportunity for further validation of the miRNAs. Modified RACE-PCR on putative targets of selected miRNA candidates will be used to identify RISC cleavage products with a 5' terminus located at the center of the putative target site of the miRNA (Llave et al., 2002). This result would strongly suggest that a given candidate miRNA enters into a RISC complex, and thus functions as would be expected for a bona fide miRNA.

Functional studies will be initiated on selected miRNAs with expression patterns and/or targets of agronomic interest, for example drought-induced or kernel-specific miRNAs. To determine the in planta function of selected miRNAs, the miRNA can be overexpressed by fusing a sequence (either cDNA or genomic) encompassing the hairpin precursor of the miRNA, plus a minimal amount of flanking sequence, to a constitutive promoter (e.g. the maize Ubiquitin promoter) and creating transgenic maize lines with this construct. Depending on the agronomic trait being studied, phenotyping can be carried out on independent T0 individuals overexpressing the miRNA. In addition, the effects of miRNA overexpression on the relevant target genes can be assessed by Northern blot and/or RT-PCR, to confirm that a predicted target is in fact a bona fide target. An independent demonstration that a given miRNA controls the expression of a given target gene is to mutate the target site present within the target gene (without changing amino acid sequence), and retransform the "miRNA-resistant" version of the target gene. This approach allows one to assess the phenotype conferred by loss of miRNA regulation, which in the majority of cases cannot be assessed by direct knockout of the miRNA (due to genetic redundancy and/or lack of an available knockout line).

Example 6

Validation of Small RNAs by Expression Profiling

Because the number of disclosed candidate miRNAs number in the thousands, validation must be performed using high-throughput procedures. Microarray technology is useful for this purpose. The flexibility and reliability of microarrays is well documented (Davison et al. (2006), *Methods in Enzymology* 411: 14-34; Axtell and Bartel (2005), *Plant Cell* 17: 1658-1673), as is their suitability for assaying the expression of many different tissues and conditions. The specific protocols for small RNA hybridization to microarrays have been available for the past couple of years. Microarrays are constructed to represent the candidate miRNAs, as well as known miRNAs already in the literature. Hybridization is carried out with labeled small RNA fractions purified from a variety of maize tissues, including different organs such as roots, leaves and flowers, and including environmental variables such as drought/pathogen stress and low nutrients. Statistical analysis of hybridization data allows one to identify candidate miRNAs displaying significant expression, and in this manner validate endogenous expression. This profiling approach also provides initial clues regarding the in vivo function of particular miRNAs, especially if their expression is tissue-specific or environmentally regulated. Further validation would involve Northern blot analysis and/or qRT-PCR on promising candidates (see Example 8).

Small RNA expression is analyzed by hybridization to a custom-designed plant miRNA expression array. Arrays are synthesized by Agilent technologies in the 2-pack 11,000 feature format. Known miRNA and candidate miRNA sequences from multiple species are represented by a series of specially designed reporter oligos. Reporters containing 0, 1 or 2 mismatches to the target sequence are designed in both the sense and antisense orientations. In addition, a duplexed reporter is added that contained two tandem copies of the antisense target sequence. Antisense duplexed and 0-mismatch reporters are used to detect miRNA expression. Antisense 1- and 2-mismatch reporters provide information on reporter specificity. Sense reporter data aids in differentiating miRNAs from small-interfering RNAs.

Total RNA is prepared using Trizol reagent (Invitrogen) and enriched for small RNAs (<200 nt) using glass fiber filters (miRvana small RNA isolation kit, Ambion). Small RNA samples are directly labeled with Cy-5 (Label IT miRNA labeling kit, Mirus Bio). Four micrograms of labeled RNA is hybridized to the custom arrays at 50° C. Hybridization, washing, scanning and feature extraction protocols follow the Agilent One-Color Microarray-Based Gene Expression Analysis protocols. To ensure reproducibility and reliability, samples are analyzed in triplicate. Data are analyzed using Rosetta Resolver, Spotfire DecisionSite, and customized spot-calling and error calculation programs.

Small RNAs are determined to be expressed if, for all three samples, the antisense duplex and O-mismatch reporters register intensities more than two standard deviations above background, but other reporters register signals at or below background intensity. These sequences are moved forward for additional validation by other techniques such as small RNA Northern blotting (Plant Cell. 2003; 15(11): 2730-2741), in-gel miRNA detection (miR-tect-IT miRNA labeling and detection kit, USB Corporation), custom Taqman miRNA assays (Applied Biosystems), and poly-adenylation assisted RT-PCR.

Example 7

Validation of Small RNAs by Expression Profiling

Tissue Source and RNA Extractions

Table 2 lists the genotypes, growth conditions and developmental stages of tissues harvested for expression profiling.

TABLE 2

| Growth and harvest conditions for profiled samples | | | | | |
|---|---|---|---|---|---|
| Sample Name | Tissue | Genotype | Stage | Growth condition | Experimental Condition |
| B73 Leaf | Leaf | B73 | VT | pot grown; screen house: Newark, DE | Tissue survey |
| Ear | Immature ear | B73 | VT | pot grown; screen house: Newark, DE | Tissue survey |
| B73 Seedling | Aerial seedling | B73 | V4 | germination paper in water; growth chamber (28 C., 14 hours light, 10 hours dark) | Tissue survey |
| 3245 Normal Nitrogen | Leaf | 3245 | V18 | field grown: Johnston, IA | Normal nitrogen |
| 3245 Low Nitrogen | Leaf | 3245 | V18 | field grown: Johnston, IA | Low nitrogen |
| 33B50 Normal Nitrogen | Leaf | 33B50 | V18 | field grown: Johnston, IA | Normal nitrogen |
| B73 Low Nitrogen | Leaf | B73 | V18 | pot grown, greenhouse | Low Nitrogen |

Harvested tissues were immediately frozen in liquid nitrogen and stored at −80 C. Tissues were homogenized to powder form while kept frozen. Total RNA was isolated from 2-5 grams of homogenized tissue by organic extraction using the manufacturer's protocol for Trizol™ Reagent (Invitrogen; Carlsbad, Calif.) or the E.Z.N.A. DNA/RNA Isolation System™ (Omega Bio-Tek; Doraville, Ga.). A fraction enriched for RNA molecules under 200 nucleotides in length was isolated from 100 micrograms total RNA using the mirVana™ miRNA Isolation Kit (Ambion; Austin Tex.), protocol IV.A: Isolation of small RNAs from total RNA samples. The total RNA and small RNA samples were analyzed on an RNA 6000 Nano Chip and Small RNA Chip (2100 Bioanalyzer, Agilent Technologies) respectively to determine the quality and concentration of the sample.

Array Design

Custom gene expression microarrays were manufactured by Agilent Technologies in the 4×44 k format. Each sixty nucleotide probe encoded two tandem bait sequences separated by a three nucleotide spacer and followed by 15 nucleotides of Agilent's generic spacer sequence. Guanine residues preceded each bait sequence. The overall probe design followed the format: 5'-G[BAIT]$_{21nt}$ATAG[BAIT]$_{21nt}$GCGTTCCGTATGTGG-3'.

Three probes were designed for each small RNA assayed: perfectly sequence matched probes (0MM) used bait sequences antisense to the query sequence; single mismatch probes (1MM) used antisense query sequences with a substitution at the tenth position from the 5' end of the sense query sequence as bait; double mismatch probes (2MM) used antisense query sequences with substitutions at the seventh and fifteenth positions from the 5' end of the sense query sequence as bait. Substitutions were made by replacing A with T, T with A, G with C, and C with G.

Small RNA Labeling

Prior to labeling, an aliquot of a spike-in control cocktail was added to 5 micrograms of each small RNA sample. Direct labeling of the RNA was achieved by incubating four micrograms of each sample with 4 microliters of the LabelIT Cy3 Reagent according to the LabelIT miRNA Labeling Kit protocol (Mirus Bio Corporation; Madison Wis.). The samples were subsequently quantitated with a spectrophotometer to measure concentration and Cy3 incorporation rates.

Array Hybridization

Each sample was hybridized to a custom Agilent oligonucleotide array overnight at 50 C in a rotating hybridization oven. The microarray slides were hybridized and washed according to Agilent Technologies One-Color Microarray-Based Gene Expression Analysis Protocol and immediately scanned with Agilent's DNA Microarray Scanner at two laser settings (100% and 10% PMT).

Data Analysis

The images were visually inspected for image artifacts and feature intensities were extracted, filtered, and normalized with Agilent's Feature Extraction Software (version 9.5.3.1). Further quality control and downstream analysis was performed using data analysis tools in Rosetta's Resolver Database (NBIC Rosetta Resolver System).

Samples were assayed as biological duplicates or triplicates. Feature intensity data was combined and normalized among replicates and within experiments using a least squares method with weighted regression of error. A brief description of the statistical methods for analysis of the miRNA microarray data, were previously reported (Luck, (2001) *Proceedings of SPIE* 4266:153-157). The analysis is based on the vector space representations of fluorescence intensities for microarrays and miRNAs. The first stage of the analysis involves the normalization of microarray intensities to adjust for variations in instrumental response between replicates. The normalization parameters are estimated by applying weighted regression to characterize the covariance between replicates. The normalized intensities for the replicates are averaged to obtain an intensity for each miRNA probe for a given tissue. Intensities for replicates are correlated, consequently the miRNA vectors are distributed about a mean line with dimensionality equal to the number of replicates. The noise in the intensity measurements is estimated by analyzing the squared deviations of the replicate vectors from the mean line. A variance function is obtained by weighted quadratic regression of the squared deviations versus mean intensity. An empirical confidence interval can then be associated with each value of averaged intensity. The confidence interval characterizes the overall noise including biological and instrumental contributions. The confidence intervals are used to estimate the significance level of observed deviations from the mean and identify outlier vectors among the replicates. Similarly the significance level for differences between means is used to identify those miRNAs that show significant changes in hybridization due to mismatched probes. The t distribution was used to estimate p-values for the difference statistics with the degrees of freedom equal to the number of replicates.

The reproducibility of each normalized signal was determined by ANOVA or t-test calculations among the biological replicates of each sample. Sequences with replicate P-values above 0.05 were considered to be sufficiently reproducible.

A t-test was performed comparing the normalized signal for each probe to the background signal in that sample. A query sequence with a 0MM-background P-value less than 0.05 was considered to be expressed significantly above background.

Two calculations were used to ensure the specificity of the 0MM signal for each query sequence. Again using the t-test, the 0MM normalized signal was compared pair-wise with the normalized signal for each of the query sequence's mismatch probes. Because P-values only indicate the significance of the difference between signals, but not which signal is greater, each 0MM signal was also required to be larger than both its cognate 1MM and 2MM signals. Any query sequence whose 0MM signal was larger than both of its cognate mismatch signals and whose 0MM-1MM and 0MM-2MM P-values were both less than 0.05 was considered to be show appropriate signal specificity. These criteria are summarized in Table 3.

TABLE 3

Criteria used to determine the reliable detection of query sequences.

| Value | Criteria |
| --- | --- |
| 0 MM replicate P-value | >0.05 |
| 0 MM-background P-value | <0.05 |
| 0 MM-1 MM P-value | <0.05 |
| 0 MM-2 MM P-value | <0.05 |
| 0 MM-1 MM | >0 |
| 0 MM-2 MM | >0 |

Detection criteria were applied to each sample independently. Query sequences meeting all the criteria outlined above were considered to have been reliably detected by the expression array and were marked as "passed," "enriched," or "highly enriched" in Table 4. A query sequence was designated as "enriched" in a given sample if it met all reliable detection criteria and its 0MM signal intensity in that sample was between 5-fold and 10-fold above the 0MM intensity for any other sample in the same experiment. "Highly enriched" sequences met all reliable detection criteria and displayed 0MM signal intensity at least 10-fold above the 0MM intensity of any other sample in the same experiment. In the two experiments that contained only a single sample ("33B50 Normal Nitrogen" and "B73 Low Nitrogen") query sequences were analyzed only for meeting reliable detection criteria—no calls as to enrichment were made. 0MM intensity scores in arbitrary and reliable detection assessments are listed by sample for each query sequence in Table 4.

Expression profile results for the first 2652 maize microRNAs from Table 1 are summarized in Table 4.

Detection of Public Domain Zea mays miRNAs

Public domain Zea mays miRNAs were included among the query sequences for use as detection standards. Due to sequence redundancy among miRNA family members, the 116 maize miRNAs published at the time of array design were fully represented by 50 unique mature miRNA sequences (Griffiths-Jones, et al. Nuc Acids Res (2006) 34:D140-D144. Release 9.0; Zhang, et al. FEBS Lett. (2006) 580:3753-62; Sunkar, et al. The Plant Cell (2005) 17:1397-1411; Johnson, et al. Nuc Acids Res (2007) 35:D829-D833). Using the reliable detection criteria outline in Table 3, 88% of public domain miRNA sequences were detected in at least one sample.

Of the six public domain miRNA sequences that failed to meet reliable detection criteria in any sample, only miR437 and miR444 failed to surpass background noise. As miR437 expression has not been assayed in maize and miR444 expression in maize is known to be weak compared to its expression in rice, low signal strength for these sequences could be expected (Sunkar, et al. The Plant Cell (2005) 17:1397-1411). That only 4% of public domain miRNAs sequences failed to surpass background signal indicated an excellent signal to noise ratio within these datasets. MiR168a/b, miR390 and miR395a/b/c surpassed background but failed to show significant difference between 0MM and 1MM signals. Although the 0MM signal was above background and distinct from its cognate mismatches, 2MM signal for miR171g was consistently higher than its 0MM signal. For the four miRNA sequences lacking signal resolution, it was impossible to conclude whether the query sequence was absent and the 0MM signal indicated cross-hybridization or whether the query sequence was present in addition to a second sequence that specifically hybridized to the mismatch probe.

Many public domain miRNAs have detectable basal expression in nearly all tissues. (Johnson, et al. Nuc Acids Res (2007) 35:D829-D833). Consistent with this, 46% of public domain miRNAs were reliably detected in all samples tested. Within the tissue comparison experiment, 78% or more of the public domain miRNAs are present in any sample. Near-ubiquitous basal expression also accounts for so few public domain miRNAs being scored as "enriched" or "highly enriched" in a single tissue or experimental condition. The reliable detection of public domain miRNAs is summarized in Table 5.

TABLE 5

Summary of the reliable detection of public domain miRNAs.

| Sample | Pass all criteria | Simple Pass | Enriched | Highly Enriched |
|---|---|---|---|---|
| MAXIMUM POSSIBLE | 100% (50) | | | |
| B73 Leaf | 84% (42) | 84% (42) | 0% (0) | 0% (0) |
| B73 Ear | 78% (39) | 76% (38) | 2% (1) | 0% (0) |
| B73 Seedling | 82% (41) | 82% (41) | 0% (0) | 0% (0) |
| All tissues in survey | 74% (37) | | | |
| One or more tissues | 88% (44) | | | |

TABLE 5-continued

Summary of the reliable detection of public domain miRNAs.

| Sample | Pass all criteria | Simple Pass | Enriched | Highly Enriched |
|---|---|---|---|---|
| 3245 Normal Nitrogen | 70% (35) | 70% (35) | 0% (0) | 0% (0) |
| 3245 Low Nitrogen | 62% (31) | 62% (31) | 0% (0) | 0% (0) |
| Both samples | 62% (31) | | | |
| 33B50 Normal Nitrogen | 56% (28) | | | |
| B73 Low Nitrogen | 78% (39) | | | |
| All samples | 46% (23) | | | |
| One or more samples | 88% (44) | | | |

Detection of Candidate miRNA Sequences

The reliable detection criteria described in Table 3 were also applied to data from probes representing the 2652 candidate miRNAs disclosed in this application (see Table 6). Only 136 or 5.1% of these candidates were reliably detected in all seven samples. Because they were cloned or sequenced from small RNA libraries, the most abundant and widely expressed miRNAs would have been among the earliest to be detected and published. Accordingly, it is reasonable that the proportion of candidate miRNAs ubiquitously detected was much smaller than that for public domain miRNAs. In absolute terms, the full validation of 136 miRNAs would approximately double the known cadre of maize miRNAs.

Since the most abundant miRNAs are expected to have been discovered and published in early RNA library searches, candidates showing extremely robust 0MM intensity scores across all or most samples should be treated with caution. Because the direct labeling technique conjugates a fluorescent molecule to each guanine residue, longer sequences are generally brighter than short sequences. The size fractionation kit used in sample preparation enriched for small RNAs from 0-200 nucleotides. Accordingly, candidates with 0MM intensity scores above 20,000 in most samples may be artifacts caused by RNA species much larger than 21 nucleotides in length.

Forty-one candidate sequences, or 1.5%, were reliably detected as enriched or highly enriched in particular samples. Strong tissue- or condition-specific detection patterns suggest these candidates may be especially useful in targeted gene silencing.

B73 was one of the maize strains used in the MPSS deep sequencing experiments that yielded the 2652 candidate miRNAs. The tissue survey samples used in the array analysis were also from B73 plants, as was an unpaired low nitrogen sample. Public domain and candidate miRNAs met reliable detection standards at higher rates in B73 samples than in other genotypes. Because public domain miRNAs showed differing pass rates between B73 and other genotypes, some of the discrepancy may be attributed to differences in growth conditions or sample handling. Nonetheless, candidate miRNAs showed a much greater disparity in reliable detection between B73 and other genotypes, raising the possibility that miRNAs can be differentially expressed in distinct genetic backgrounds.

TABLE 6

Summary of the reliable detection of candidate miRNAs.

| Sample | Pass all criteria | Simple Pass | Enriched | Highly Enriched |
|---|---|---|---|---|
| MAXIMUM POSSIBLE | 100.0% (2652) | | | |
| B73 Leaf | 31.7% (841) | 31.1% (824) | 0.1% (3) | 0.5% (14) |
| B73 Ear | 62.0% (1645) | 61.3% (1626) | 0.8% (20) | 0.2% (6) |
| B73 Seedling | 42.2% (1120) | 42.2% (1118) | 0.1% (2) | 0.0% (1) |
| All tissues in survey | 27.6% (731) | | | |
| One or more tissues | 64.9% (1722) | | | |
| 3245 Normal Nitrogen | 12.9% (343) | 12.9% (342) | 0.0% (0) | 0.0% (1) |
| 3245 Low Nitrogen | 9.4% (250) | 9.4% (250) | 0.0% (0) | 0.0% (0) |
| Both samples | 9.2% (243) | | | |
| 33B50 Normal Nitrogen | 8.1% (216) | | | |
| B73 Low Nitrogen | 20.4% (540) | | | |
| All samples above | 5.1% (136) | | | |
| One or more samples | 65.6% (1739) | | | |

Example 8

Validation of Small RNAs by Poly-Adenylation Assisted RT-PCR

The miRNA expression array and analysis procedures described in Example 7 can be used to evaluate candidate miRNA detectability and expression levels in additional samples, including but not limited to: additional profiling of developmentally staged organs or tissues; tissues from mutant strains defective in miRNA and small RNA biogenesis; tissues from plants exposed to biotic stress such as pathogens, pests, or weed pressure; tissues from plants exposed to abiotic stresses such as drought, heat, or cold; and tissues from plants subjected to nutrient stress such as low nitrogen.

Candidates can be prioritized for individual characterization based on the number of samples in which they were reliably detected, the utility potential of putative targets, and temporal, spatial and conditional expression patterns. Well known characterization methods include, but are not limited to, quantitative RT-PCR, Northern blotting, in situ hybridization, reporter silencing assays, and modified 5' RACE on putative targets.

As an example, small RNAs are analyzed using a modified version of the Shi & Chiang protocol that allows for the amplification of RNA fragments that do not have native poly (A) tails (Biotechniques. 2005; 39(4):519-25). DNA is removed from total RNA samples prepared with Trizol reagent (Invitrogen) by digestion with recombinant DNaseI (Ambion). Following ethanol precipitation of the RNA, the material is poly-adenylated using E. coli Poly(A) polymerase (Poly(A) Tailing Kit, Ambion).

First-strand DNA synthesis is accomplished with SuperScriptIII reverse transcriptase and supplied poly(T) primers (GeneRacer Kit, Invitrogen). Subsequent amplification by end-point PCR uses low annealing temperatures (56° C.) and short extension times (30 seconds). The GeneRacer 3' Primer (GeneRacer Kit, Invitrogen) is used as reverse primer and a sense, DNA version of the small RNA of interest is used as a forward primer. The presence of the diagnostic ~81 mer PCR product is assessed by visualizing PCR products with ethidium bromide on 10% acrylamide TBE gels (Criterion gels, BioRad).

Example 9

Selective Regulation of Transgenes with MicroRNAs

Because each candidate miRNA has the potential to recognize and negatively regulate a complementary sequence (i.e. "target site"), it is believed that target sites for these candidate miRNAs will serve as useful cis-acting regulatory sequences in transgenic constructs (Parizotto et al. (2004) Genes Dev 18: 2237-2242). This is especially true when the miRNA displays a precise tissue-specific or conditional pattern of expression. For example, to express a particular gene of interest in the shoot but not in the root, the target site of a root-specific miRNA is fused to the coding sequence of said gene of interest. In this manner, even if the gene of interest is driven by a constitutive promoter, the transcript should only accumulate in the shoot and not in the root, because the endogenous root-specific miRNA will recognize the attached target site and silence the gene's expression in the root.

To test this idea, miRNAs displaying tissue-specific expression are identified (see Example 7). Ideally, biologically relevant targets can be found bioinformatically and validated by the RACE cleavage assay; however, a sequence that is perfectly complementary to the miRNA should also suffice. The sequence designated as target site is fused to the 5' or 3' end of a suitable reporter gene that is driven by a constitutive promoter, and transgenic plants are generated. A pattern of expression that is the opposite of the tissue-specific miRNA pattern is taken as evidence that the target site is working as a cis regulatory element. This type of cis regulation allows further refinement of transgene expression patterns, such that "leaky" promoters (e.g. with small amounts of gene expression in undesirable tissues or conditions) are fine tuned and true tissue-specificity is achieved.

One example of a miRNA that has a stage-specific pattern of expression is miR172. In young Arabidopsis seedlings, miR172 is undetectable, whereas in more mature seedlings it is at higher levels, and this higher expression persists after the transition to flowering (Aukerman and Sakai (2003) Plant Cell 15:2730-41). Addition of the miR172 target site to a heterologous gene in a transgenic construct should therefore allow the transgene to be turned on in early seedling development, and then downregulated later on. To test this concept, the target sequence for miR172 is fused to the 3' end of the coding sequence for coral reef yellow fluorescent protein (ZS-yellow, Clonetech). As a negative control, a mutated version of the miR172 target site is separately fused to ZS-yellow, and both gene cassettes are separately placed under the control of the constitutive 35S promoter in a standard binary vector. These constructs are transformed into *Arabidopsis* (ecotype Col-0), and also into the rdr6 mutant if the levels of transgene silencing (independent of miRNA regulation) are too high. The expected result is that levels of ZS-yellow will be high in young transgenic seedlings containing the ZS-yellow/wild-type target site, and much lower as the plants mature. On the other hand, transgenic plants containing the ZS-yellow/mutated target site should not display this stage-specific downregulation.

To extend this analysis to maize, a target site for one of the maize miRNAs in this application's sequence listing, (SEQ ID NO:116; 5'-TTAGATGACCATCAGCAAAC-3') is useful. This particular miRNA is expressed at high levels in maize endosperm, and at much lower levels in other tissues. The target gene is EB158863, and the target site has two mismatches with the miRNA at the 3' end of the miRNA. The target site is fused to the 3' end of ZS-yellow, and this construct is placed under the control of the maize ubiquitin promoter. The expression construct is inserted into a suitable vector for maize transformation. A negative control construct containing a mutated version of the target site is also be made. Both constructs are transformed into maize embryogenic callus, and transgenic plants are selected. The expected result is that the levels of ZS-yellow will be high in most parts of the plants that contain the ZS-yellow/wild-type target site, but much lower in the endosperm. On the other hand, transgenic plants containing the ZS-yellow/mutated target site should not display this endosperm-preferred downregulation.

A reciprocal result is also possible in these types of experiments. The enriched/highly enriched calls shown in Example 7 were based on condition specificity or enhancement. Therefore the summaries were weighted for detection versus no detection. It is just as likely that particular microRNAs are depleted in a specific tissue rather than being enhanced in a specific tissue. This would allow target genes to be generally repressed and then expressed in a limited fashion in those tissues where the particular microRNA is under-expressed.

In both experiments described above, a pattern of expression that is the opposite of the tissue-specific miRNA pattern will be taken as evidence that the target site under study is working as a cis regulatory element. Utilizing these novel cis elements in combination with a wide variety of promoter elements allows for expression of transgenes in very specific patterns or stages during plant growth and development. For example, this type of cis regulation by miRNA targets would allow further refinement of transgene expression patterns, such that "leaky" promoters (e.g. with small amounts of gene expression in undesirable tissues or conditions) could be fine tuned and true tissue-specificity could be achieved. It is also envisioned that multiple miRNA targets could be incorporated in concert on a single expressed transgene. Multiple miRNA targets with different patterns of regulation and control could impart novel modes of regulation on transgene expression.

Example 10

Transgene Abundance May Affect Regulation by MicroRNAs

To test the potential for combinatorial control of transgenes by multiple miRNAs, the following experiment was performed. The ZS-yellow coding region was separately fused to either a target sequence for AtmiR827 at the 5' end, or to a target sequence for AtmiR397 at the 3' end ("single site constructs"). In a third construct, both target sequences were fused to ZS-yellow coding sequence, in the same positions as the single site constructs, thus creating a "double site construct." Previous data showed that AtmiR827 was specifically expressed in hydathodes, based upon analyses of AtmiR827 promoter-GUS histochemical assays. Therefore, a single site transgene construct containing the target site for AtmiR827 would be under the control of the endogenous miRNA, and might be expected to give rise to reduced expression of the transgene in hydathodes, when compared to a "no site" control construct. Likewise, microarray analysis had suggested that AtmiR397 was preferentially expressed in the root, and therefore a construct containing the target site for AtmiR397 might be expected to give rise to reduced expression of the transgene in the root, when compared to a "no site" control. The double site construct might be expected to behave as the sum of both single site constructs, giving rise to reduced expression in both the hydathode and root.

All three modified ZS-yellow sequences were separately placed under the control of the constitutive 35S promoter, and an unmodified ZS-yellow sequence was also separately fused to 35S as the "no site" control, in the binary vector pBC (Promega; Madison, Wis.). Both single site constructs, the double site construct, and the "no site" control construct were transformed into *Arabidopsis* using "floral dip" transformation (Clough and Bent (1998) *Plant J* 16:735-43) and T1 seeds were identified that expressed YFP from the ZS-yellow transgene. The T1 seeds were germinated on agar plates, and monitored for YFP expression starting at 5 days after germination. There were no observed differences in the expression pattern between the four constructs. More specifically, there was no observed reduction of YFP expression in the hydathodes in plants containing ZS-yellow fused to the target site for AtmiR827, nor was there a reduction of YFP expression in the roots of plants containing ZS-yellow fused to the target site for AtmiR397, when compared to ZS-yellow alone. Plants containing both sites fused to ZS-yellow likewise showed no effect relative to ZS-yellow alone. It is possible that the levels of endogenous AtmiR827 and AtmiR397 are too low relative to the levels of target-linked ZS-yellow to have achieved the desired downregulation in the relevant tissues. Both miRNAs are in general not very abundant, compared to commonly studied miRNAs like miR171 or miR156; whereas the target gene sequences in this experiment were driven by a strong viral promoter (35S). It should be noted that the only group that has reported transgene downregulation mediated by an endogenous miRNA (Parizotto et al. (2004) *Genes Dev* 18: 2237-2242) utilized miR171, a highly abundant miRNA, to downregulate a 35S-driven transgene containing the cognate target site.

Example 11

Selective Regulation of Transgenes with MicroRNAs of Comparable Abundance

YFP transcripts incorporating AtmiR827 and Atmir397 target sites may not have exhibited altered expression due to the extremely low abundance of those miRNAs in planta, especially when compared to the high levels of YFP mRNA likely produced by the 35S promoter. Therefore, target sites from more abundant miRNAs might circumvent this potential problem. To this end, the ZS-yellow coding region can be separately fused to either a target sequence for AtmiR171 at the 5' end, or to a target sequence for AtmiR156 at the 3' end ("single site constructs"). In a third construct, both target sequences will be fused to ZS-yellow coding sequence, in the same positions as the single site constructs, thus creating a "double site" construct. Both AtmiR171 and AtmiR156 are relatively abundant microRNAs, and are expressed in a variety of tissues. In the gynoecium, AtmiR171 is expressed in the carpel valves but absent from the replum, style and stigma; this pattern is reciprocal to that seen for a reporter construct ("sensor construct") containing the AtmiR171 target site (Parizotto et al. (2004) *Genes Dev* 18: 2237-2242). In contrast, AtmiR156 expression in the gynoecium is limited to the style (Rebecca Schwab, 2006, thesis from University of Tubingen), and thus the single site construct containing an AtmiR156 target site fused to ZS-yellow should have YFP expression in all parts of the gynoecium except the style. The double site construct with ZS-yellow would be expected to give rise to YFP expression only in the areas where both miRNAs are absent, i.e. the replum and stigma. One would expect the double site construct to behave as the sum of both single site constructs, with regards to YFP expression in the gynoecium.

Example 12

Trans-Acting miRNA Silencing

One can envision using tissue- or stage-specific miRNAs to silence a gene of interest only in a particular tissue or development stage of the organism, utilizing an artificial transacting sRNA (ta-sRNA) construct. The objective in this case is to generate artificial ta-siRNAs in a tissue- or stage-specific manner, by using a miRNA target corresponding to a tissue- or stage-specific miRNA as the trigger sequence ("trigger" refers to the target sequence that initiates production of the downstream ta-siRNAs). For example, if it were desired to silence a gene in the seeds of plants, one would choose as a trigger sequence the target sequence of a miRNA present only in the seeds. Such constructs are generated as follows:

A chimeric polynucleotide is constructed in which the target site for a tissue- or stage-specific miRNA is used as a trigger sequence and is operably linked to the 5' end of a silencer sequence. The silencer sequence comprises a synthetic DNA fragment containing 5 repeated copies of a 21 nucleotide segment complementary to the *Arabidopsis* fatty acid desaturase 2 (FAD2) gene with the sequence [5'-TTGCTTTCTTCAGATCTCCCA-3'; SEQ ID NO:7958]. The trigger sequence complementary to the miRNA is followed by 11 nucleotides such that the miRNA cleavage site is separated by 21 nucleotides from the first of the 21 nucleotide FAD2 segments. Sequences flanking the trigger and silencer are derived from the TAS1c locus (Allen et al. (2005) *Cell* 121:207-21). The 35S promoter and leader sequence (Odell (1985) *Nature* 313: 810-812) are attached to the 5' end of the chimeric construct and the phaseolin transcriptional terminator (Barr et al. (2004) *Molecular Breeding* 13: 345-356) to the 3' end. The entire chimeric polynucleotide is inserted into the standard binary vector pBE851 (Aukerman and Sakai (2003) *Plant Cell* 15:2730-41) and transformed into *Arabidopsis* using the method of Clough and Bent (1998) *Plant Journal* 16:735-43. As a control, the exact same construct is made but with 3 nucleotides of the miRNA target site mutated. Transgenic plants containing the experimental construct are monitored for silencing of the FAD2 gene using fatty acid analysis (Browse et al. (1986) *Analytical Biochemistry* 152: 141-145) and compared to control plants. Silencing may be scored as a detectable reduction in transcript level and/or a reduction in the gene products produced by those transcripts.

It is believed that any of the targets of microRNAs of the present invention could be useful as the tissue- or stage-specific trigger sequences. In addition, concatemers of miRNA sequences (such as those found in SEQ ID NO:7957 or SEQ ID NO:8427) are also useful as silencer sequences which would down-regulate their endogenous targets and/or the gene products of those targets in a pattern directed by the trigger sequence. Using different combinations of miRNA target sequences one could conceivably alter the expression patterns of multiple genes with a single construct.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08981181B2). An electronic copy of the "Sequence Listing" will also be available from the USPTO upon request and payment of the fee set forth in 37 CFR 1.19(b)(3).

What is claimed is:

1. A recombinant DNA construct comprising a microRNA consisting of the sequence set forth in SEQ ID NO:510 operably linked to at least one heterologous regulatory sequence, wherein said recombinant DNA construct when expressed in a plant cell produces the microRNA.

2. A plant, plant tissue, or a plant cell comprising in its genome the recombinant DNA construct of claim 1.

3. Transgenic seeds or transgenic progeny plants obtained from the plant of claim 2, wherein said transgenic seeds or transgenic progeny plants comprise the recombinant DNA construct.

4. A method for altering expression of a stably introduced nucleotide sequence in a plant comprising:

a) transforming a plant with the recombinant DNA construct of claim 1; and b) selecting a transformed plant which comprises the recombinant DNA construct of part (a) in its genome and which has altered expression of the stably introduced nucleotide sequence;

wherein the stably introduced nucleotide sequence comprises a sequence capable of hybridizing to the polynucleotide sequence set forth in SEQ ID NO:510.

* * * * *